(12) United States Patent
Bar-El et al.

(10) Patent No.: US 11,484,470 B2
(45) Date of Patent: Nov. 1, 2022

(54) LIQUID TRANSFER DEVICE WITH DUAL LUMEN IV SPIKE

(71) Applicant: West Pharma. Services IL, Ltd., Ra'anana (IL)

(72) Inventors: Yossi Bar-El, Beit Arye (IL); Elisheva Fabrikant, Herzliya (IL); Niv Ben Shalom, Netanya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 16/982,410

(22) PCT Filed: Jan. 13, 2020

(86) PCT No.: PCT/IL2020/050048
§ 371 (c)(1),
(2) Date: Sep. 18, 2020

(87) PCT Pub. No.: WO2020/222220
PCT Pub. Date: Nov. 5, 2020

(65) Prior Publication Data
US 2022/0047458 A1    Feb. 17, 2022

Related U.S. Application Data

(60) Provisional application No. 62/840,620, filed on Apr. 30, 2019.

(51) Int. Cl.
*A61J 1/20* (2006.01)
*A61J 1/10* (2006.01)
*A61M 5/162* (2006.01)

(52) U.S. Cl.
CPC .............. *A61J 1/2089* (2013.01); *A61J 1/10* (2013.01); *A61J 1/2013* (2015.05); *A61J 1/2037* (2015.05); *A61J 1/2058* (2015.05); *A61M 5/162* (2013.01)

(58) Field of Classification Search
CPC    A61J 1/2089; A61J 1/10; A61J 1/2013; A61J 1/2037; A61J 1/2058; A61M 5/162
See application file for complete search history.

(56) References Cited

U.S. PATENT DOCUMENTS 62,333 A     2/1867  Hall
247,975 A   10/1881  Wickes
(Continued)

FOREIGN PATENT DOCUMENTS

CA    2946559 A1    10/2015
CN    1636605 A     7/2005
(Continued)

OTHER PUBLICATIONS

Int'l Preliminary Report on Patentability dated Aug. 24, 2015 in Int'l Application No. PCT/IL2014/050405.
(Continued)

*Primary Examiner* — Ariana Zimbouski
(74) *Attorney, Agent, or Firm* — Blank Rome LLP

(57) ABSTRACT

A liquid transfer device includes a monolithic trifurcated connector body defining a barrel at a first end thereof, a single IV spike at a second end thereof and a vial adapter lumen at a third end thereof. An IV port is connected to the barrel. The single IV spike has a first IV spike lumen fluidly connected at a proximal end thereof with only the vial adapter lumen via the trifurcated connector body and a second IV spike lumen fluidly connected at a proximal end thereof with only the IV port via the trifurcated connector body, thereby separating fluid communication between the vial adapter and the single IV spike from fluid communication between the IV port and the single IV spike.

18 Claims, 14 Drawing Sheets

(56) References Cited

U.S. PATENT DOCUMENTS

| | | |
|---|---|---|
| 254,444 A | 2/1882 | Vogel et al. |
| 300,060 A | 6/1884 | Ford |
| 1,021,681 A | 3/1912 | Jennings |
| 1,704,817 A | 3/1929 | Ayers |
| 1,930,944 A | 10/1933 | Schmitz, Jr. |
| 2,326,490 A | 8/1943 | Perelson |
| 2,560,162 A | 7/1951 | Ferguson |
| 2,748,769 A | 6/1956 | Jennie |
| 2,830,587 A | 4/1958 | James |
| 2,931,668 A | 4/1960 | Baley |
| 2,968,497 A | 1/1961 | Mervyn |
| 3,059,643 A | 10/1962 | Barton |
| D198,499 S | 6/1964 | Andrew et al. |
| 3,225,763 A | 12/1965 | Waterman |
| 3,277,893 A | 10/1966 | Clark |
| 3,308,822 A | 3/1967 | De Luca |
| 3,484,849 A | 12/1969 | Huebner et al. |
| 3,618,637 A | 11/1971 | Santomieri |
| 3,757,981 A | 9/1973 | Harris, Sr. et al. |
| D229,518 S | 12/1973 | Bujan |
| 3,782,365 A | 1/1974 | Pinna |
| 3,788,524 A | 1/1974 | Davis et al. |
| 3,822,700 A | 7/1974 | Pennington |
| 3,826,261 A | 7/1974 | Killinger |
| 3,872,992 A | 3/1975 | Larson |
| 3,885,607 A | 5/1975 | Peltier |
| 3,938,520 A | 2/1976 | Scislowicz et al. |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,026,128 A | 5/1977 | Blanco |
| 4,051,852 A | 10/1977 | Villar |
| D247,975 S | 5/1978 | Luther |
| D248,568 S | 7/1978 | Ismach |
| 4,109,670 A | 8/1978 | Slagel |
| 4,121,585 A | 10/1978 | Becker, Jr. |
| 4,161,178 A | 7/1979 | Genese |
| 4,187,848 A | 2/1980 | Taylor |
| D254,444 S | 3/1980 | Levine |
| 4,203,067 A | 5/1980 | Bollongino et al. |
| 4,203,443 A | 5/1980 | Genese |
| 4,210,173 A | 7/1980 | Choksi et al. |
| D257,286 S | 10/1980 | Folkman |
| 4,253,501 A | 3/1981 | Ogle |
| 4,262,671 A | 4/1981 | Kersten |
| 4,296,786 A | 10/1981 | Brignola |
| 4,303,067 A | 12/1981 | Connolly et al. |
| 4,312,349 A | 1/1982 | Cohen |
| 4,314,586 A | 2/1982 | Folkman |
| 4,328,802 A | 5/1982 | Curley et al. |
| 4,335,717 A | 6/1982 | Bujan et al. |
| D267,199 S | 12/1982 | Koenig |
| 4,364,387 A | 12/1982 | Larkin |
| 4,376,634 A | 3/1983 | Prior et al. |
| D268,871 S | 5/1983 | Benham et al. |
| 4,392,850 A | 7/1983 | Elias et al. |
| D270,282 S | 8/1983 | Gross |
| 4,410,321 A | 10/1983 | Pearson et al. |
| 4,411,662 A | 10/1983 | Pearson |
| D271,421 S | 11/1983 | Fetterman |
| 4,434,823 A | 3/1984 | Hudspith |
| 4,465,471 A | 8/1984 | Harris et al. |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,534,758 A | 8/1985 | Akers et al. |
| 4,561,445 A | 12/1985 | Berke et al. |
| 4,564,054 A | 1/1986 | Gustavsson |
| 4,573,993 A | 3/1986 | Hoag et al. |
| 4,576,211 A | 3/1986 | Valentini et al. |
| 4,581,014 A | 4/1986 | Millerd et al. |
| 4,585,446 A | 4/1986 | Kempf |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,675,020 A | 6/1987 | Mcphee |
| 4,676,530 A | 6/1987 | Nordgren et al. |
| D291,490 S | 8/1987 | Raines |
| 4,683,975 A | 8/1987 | Booth et al. |
| 4,697,622 A | 10/1987 | Swift et al. |
| 4,721,133 A | 1/1988 | Sundblom |
| 4,729,401 A | 3/1988 | Raines |
| 4,735,608 A | 4/1988 | Sardam |
| 4,743,229 A | 5/1988 | Chu |
| 4,743,243 A | 5/1988 | Vaillancourt |
| 4,752,292 A | 6/1988 | Lopez et al. |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,797,898 A | 1/1989 | Martinez |
| D300,060 S | 2/1989 | Molgaard-Nielsen |
| 4,804,366 A | 2/1989 | Zdeb et al. |
| 4,826,492 A | 5/1989 | Magasi |
| 4,832,690 A | 5/1989 | Kuu |
| 4,834,152 A | 5/1989 | Howson et al. |
| 4,834,744 A | 5/1989 | Ritson |
| D303,013 S | 8/1989 | Konopka |
| 4,857,062 A | 8/1989 | Russell |
| 4,865,592 A | 9/1989 | Rycroft |
| 4,871,463 A | 10/1989 | Taylor et al. |
| 4,898,209 A | 2/1990 | Zdeb |
| 4,909,290 A | 3/1990 | Coccia |
| 4,919,596 A | 4/1990 | Slate et al. |
| 4,927,423 A | 5/1990 | Malmborg |
| 4,931,040 A | 6/1990 | Haber et al. |
| 4,932,944 A | 6/1990 | Jagger et al. |
| 4,967,797 A | 11/1990 | Manska |
| D314,050 S | 1/1991 | Sone |
| D314,622 S | 2/1991 | Andersson et al. |
| 4,997,430 A | 3/1991 | Van Der Heiden et al. |
| 5,006,114 A | 4/1991 | Rogers et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,125,915 A | 6/1992 | Berry et al. |
| D328,788 S | 8/1992 | Sagae et al. |
| D331,281 S | 11/1992 | Levine |
| 5,171,230 A | 12/1992 | Eland et al. |
| 5,181,508 A | 1/1993 | Poole, Jr. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| D337,828 S | 7/1993 | Gordon |
| 5,232,029 A | 8/1993 | Knox et al. |
| 5,232,109 A | 8/1993 | Tirrell et al. |
| 5,242,432 A | 9/1993 | Defrank |
| 5,247,972 A | 9/1993 | Tetreault |
| D341,420 S | 11/1993 | Conn |
| 5,269,768 A | 12/1993 | Cheung |
| 5,270,219 A | 12/1993 | Decastro et al. |
| 5,279,576 A | 1/1994 | Loo et al. |
| 5,288,290 A | 2/1994 | Brody |

(56) References Cited

U.S. PATENT DOCUMENTS

| | | |
|---|---|---|
| 5,300,034 A | 4/1994 | Behnke et al. |
| 5,301,685 A | 4/1994 | Guirguis |
| 5,304,163 A | 4/1994 | Bonnici et al. |
| 5,304,165 A | 4/1994 | Haber et al. |
| 5,308,483 A | 5/1994 | Sklar et al. |
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,348,544 A | 9/1994 | Sweeney et al. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,482,446 A | 1/1996 | Williamson et al. |
| 5,492,147 A | 2/1996 | Challender et al. |
| 5,496,274 A | 3/1996 | Graves et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | Mcphee et al. |
| 5,527,306 A | 6/1996 | Haining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,686 A | 10/1996 | Sauer et al. |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,658,133 A | 8/1997 | Anderson et al. |
| 5,672,160 A | 9/1997 | Oesterlind et al. |
| 5,674,195 A | 10/1997 | Truthan |
| 5,676,346 A | 10/1997 | Leinsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| 5,728,087 A | 3/1998 | Niedospial |
| D393,722 S | 4/1998 | Fangrow et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow et al. |
| 5,814,020 A | 9/1998 | Gross |
| D399,558 S | 10/1998 | Guala et al. |
| D399,559 S | 10/1998 | Molina |
| 5,817,082 A | 10/1998 | Niedospial et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| D403,398 S | 12/1998 | Guala et al. |
| 5,853,406 A | 12/1998 | Masuda et al. |
| D405,522 S | 2/1999 | Hoenig et al. |
| 5,868,710 A | 2/1999 | Battiato et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,941,850 A | 8/1999 | Shah et al. |
| 5,944,700 A | 8/1999 | Nguyen et al. |
| D414,562 S | 9/1999 | Tajima |
| 5,954,104 A | 9/1999 | Daubert et al. |
| 5,968,022 A | 10/1999 | Saito |
| 5,971,181 A | 10/1999 | Niedospial et al. |
| 5,971,965 A | 10/1999 | Mayer |
| D416,086 S | 11/1999 | Parris et al. |
| 5,989,237 A | 11/1999 | Fowles et al. |
| D417,733 S | 12/1999 | Howell et al. |
| 6,003,566 A | 12/1999 | Thibault et al. |
| 6,004,278 A | 12/1999 | Botich |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote et al. |
| D422,357 S | 4/2000 | Niedospial et al. |
| 6,053,899 A | 4/2000 | Slanda et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |

(56) References Cited

U.S. PATENT DOCUMENTS

| | | |
|---|---|---|
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |
| 6,139,534 A | 10/2000 | Niedospial et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial et al. |
| 6,159,192 A | 12/2000 | Fowles et al. |
| 6,162,199 A | 12/2000 | Geringer |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | Dejonge |
| 6,174,304 B1 | 1/2001 | Weston |
| 6,179,822 B1 | 1/2001 | Niedospial |
| 6,179,823 B1 | 1/2001 | Niedospial, Jr. |
| 6,186,997 B1 | 2/2001 | Gabbard et al. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| D453,221 S | 1/2002 | Haytman et al. |
| 6,343,629 B1 | 2/2002 | Wessman et al. |
| 6,348,044 B1 | 2/2002 | Coletti et al. |
| 6,358,236 B1 | 3/2002 | Defoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,419,696 B1 | 7/2002 | Ortiz et al. |
| 6,440,107 B1 | 8/2002 | Trombley, III et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial et al. |
| 6,503,240 B1 | 1/2003 | Niedospial et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial |
| 6,551,299 B2 | 4/2003 | Miyoshi et al. |
| 6,558,365 B2 | 5/2003 | Zinger et al. |
| 6,569,196 B1 | 5/2003 | Vesely |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,581,648 B1 | 6/2003 | Zolentroff et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,632,201 B1 | 10/2003 | Mathias et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,699,232 B2 | 3/2004 | Hart et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Arnissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | Mcfarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,953,450 B2 | 10/2005 | Baldwin et al. |
| 6,957,745 B2 | 10/2005 | Thibault et al. |
| 6,960,164 B2 | 11/2005 | O'Heeron |
| 6,964,684 B2 | 11/2005 | Ortiz et al. |
| 6,972,002 B2 | 12/2005 | Thorne |
| 6,979,318 B1 | 12/2005 | Mcdonald et al. |
| RE38,996 E | 2/2006 | Crawford et al. |
| 6,994,315 B2 | 2/2006 | Ryan et al. |
| 6,997,916 B2 | 2/2006 | Simas et al. |
| 6,997,917 B2 | 2/2006 | Niedospial et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,097,637 B2 | 8/2006 | Triplett et al. |
| 7,100,890 B2 | 9/2006 | Cote et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| D546,450 S | 7/2007 | Wolf |
| 7,241,285 B1 | 7/2007 | Dikeman |
| 7,294,122 B2 | 11/2007 | Kubo et al. |
| 7,306,199 B2 | 12/2007 | Leinsing et al. |
| D560,815 S | 1/2008 | Tajima |

(56) References Cited

U.S. PATENT DOCUMENTS

| | | |
|---|---|---|
| D561,348 S | 2/2008 | Zinger et al. |
| 7,326,188 B1 | 2/2008 | Russell et al. |
| 7,326,194 B2 | 2/2008 | Zinger et al. |
| 7,335,213 B1 | 2/2008 | Hyde et al. |
| 7,350,764 B2 | 4/2008 | Raybuck |
| 7,354,422 B2 | 4/2008 | Riesenberger et al. |
| 7,354,427 B2 | 4/2008 | Fangrow |
| D573,250 S | 7/2008 | MacRae et al. |
| D575,314 S | 8/2008 | Hind |
| 7,425,209 B2 | 9/2008 | Fowles et al. |
| 7,435,246 B2 | 10/2008 | Zihlmann |
| D580,558 S | 11/2008 | Shigesada et al. |
| D581,529 S | 11/2008 | Moehle et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,500,961 B2 | 3/2009 | Nemoto |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,569,062 B1 | 8/2009 | Kuehn et al. |
| D604,837 S | 11/2009 | Crawford et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| D609,804 S | 2/2010 | Uchida et al. |
| 7,654,995 B2 | 2/2010 | Warren et al. |
| 7,670,326 B2 | 3/2010 | Shemesh |
| 7,695,445 B2 | 4/2010 | Yuki |
| 7,703,483 B2 | 4/2010 | Hartman et al. |
| 7,704,229 B2 | 4/2010 | Moberg et al. |
| 7,704,236 B2 | 4/2010 | Denolly |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosier et al. |
| 7,744,581 B2 | 6/2010 | Wallen et al. |
| 7,757,901 B2 | 7/2010 | Welp |
| 7,758,082 B2 | 7/2010 | Weigel et al. |
| 7,758,560 B2 | 7/2010 | Connell et al. |
| 7,762,524 B2 | 7/2010 | Cawthon et al. |
| 7,766,304 B2 | 8/2010 | Phillips |
| 7,771,383 B2 | 8/2010 | Truitt et al. |
| D624,641 S | 9/2010 | Boclet |
| 7,799,009 B2 | 9/2010 | Niedospial et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| 7,883,499 B2 | 2/2011 | Fangrow |
| 7,887,583 B2 | 2/2011 | Macoviak |
| 7,895,216 B2 | 2/2011 | Longshaw et al. |
| D634,007 S | 3/2011 | Zinger et al. |
| 7,896,849 B2 | 3/2011 | Delay |
| 7,900,659 B2 | 3/2011 | Whitley et al. |
| 7,914,499 B2 | 3/2011 | Gonnelli et al. |
| D637,713 S | 5/2011 | Nord et al. |
| 7,963,954 B2 | 6/2011 | Kavazov |
| D641,080 S | 7/2011 | Zinger et al. |
| 7,985,216 B2 | 7/2011 | Daily et al. |
| D644,104 S | 8/2011 | Maeda et al. |
| 7,993,328 B2 | 8/2011 | Whitley |
| 8,007,461 B2 | 8/2011 | Huo et al. |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,025,683 B2 | 9/2011 | Morrison |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosier et al. |
| 8,122,923 B2 | 2/2012 | Kraus et al. |
| 8,123,736 B2 | 2/2012 | Kraushaar et al. |
| D655,071 S | 3/2012 | Davila |
| D657,461 S | 4/2012 | Schembre et al. |
| 8,152,779 B2 | 4/2012 | Cabiri |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| D671,654 S | 11/2012 | Akamatsu et al. |
| 8,317,741 B2 | 11/2012 | Kraushaar |
| 8,328,784 B2 | 12/2012 | Jensen et al. |
| D673,673 S | 1/2013 | Wang |
| D674,084 S | 1/2013 | Linnenschmidt |
| D674,088 S | 1/2013 | Lev et al. |
| 8,348,898 B2 | 1/2013 | Cabiri |
| D681,230 S | 4/2013 | Mosier et al. |
| 8,418,690 B2 | 4/2013 | Power et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D689,605 S | 9/2013 | Bellenoit |
| D690,009 S | 9/2013 | Schembre et al. |
| D690,418 S | 9/2013 | Rosenquist |
| 8,523,837 B2 | 9/2013 | Wiggins et al. |
| D691,264 S | 10/2013 | Dallemagne et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,636,689 B2 | 1/2014 | Halili et al. |
| D703,812 S * | 4/2014 | Cederschiold ............... D24/129 |
| 8,684,992 B2 | 4/2014 | Sullivan et al. |
| 8,684,994 B2 | 4/2014 | Lev et al. |
| 8,752,598 B2 | 6/2014 | Denenburg et al. |
| D714,935 S | 10/2014 | Nishioka et al. |
| D717,406 S | 11/2014 | Stanley et al. |
| D717,948 S | 11/2014 | Strong et al. |
| D719,650 S | 12/2014 | Arinobe et al. |
| D720,067 S | 12/2014 | Rosenquist |

(56) References Cited

U.S. PATENT DOCUMENTS

| | | | |
|---|---|---|---|
| D720,451 S | 12/2014 | Denenburg et al. |
| D720,452 S | 12/2014 | Jordan |
| 8,900,212 B2 | 12/2014 | Kubo |
| 8,905,994 B1 | 12/2014 | Lev et al. |
| 8,915,882 B2 | 12/2014 | Cabiri |
| D720,850 S | 1/2015 | Hsia et al. |
| 8,986,370 B2 | 3/2015 | Annest |
| 9,011,522 B2 | 4/2015 | Annest |
| D732,660 S | 6/2015 | Ohashi |
| D732,664 S | 6/2015 | Woehr et al. |
| D733,291 S | 6/2015 | Wang |
| D733,292 S | 6/2015 | Rogers |
| D733,293 S | 6/2015 | Rogers |
| 9,072,827 B2 | 7/2015 | Cabiri |
| D738,494 S | 9/2015 | Kashmirian |
| D741,457 S | 10/2015 | Guest |
| 9,149,575 B2 | 10/2015 | Cabiri |
| D750,235 S | 2/2016 | Maurice |
| 9,254,242 B2 | 2/2016 | Mueller et al. |
| D757,933 S | 5/2016 | Lev et al. |
| 9,393,365 B2 | 7/2016 | Cabiri |
| D765,837 S | 9/2016 | Lev et al. |
| D767,124 S | 9/2016 | Lev et al. |
| 9,486,391 B2 | 11/2016 | Shemesh |
| 9,492,610 B2 | 11/2016 | Cabiri |
| 9,511,190 B2 | 12/2016 | Cabiri |
| 9,522,234 B2 | 12/2016 | Cabiri |
| D794,183 S | 8/2017 | Lev et al. |
| 9,763,855 B2 | 9/2017 | Fangrow |
| D833,599 S | 11/2018 | Nilsson et al. |
| D836,324 S | 12/2018 | Michalski |
| 10,206,854 B2 | 2/2019 | Wu et al. |
| D849,936 S | 5/2019 | Allard |
| D851,240 S | 6/2019 | Baid |
| 10,413,662 B2 | 9/2019 | Yeh et al. |
| D881,389 S | 4/2020 | Wang et al. |
| D881,390 S | 4/2020 | Wang et al. |
| 10,772,798 B2 | 9/2020 | Lev et al. |
| D903,836 S | 12/2020 | Pak et al. |
| D923,782 S | 6/2021 | Lev et al. |
| D923,812 S | 6/2021 | Ben Shalom |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0047150 A1 | 11/2001 | Chobotov |
| 2001/0051793 A1 | 12/2001 | Weston |
| 2002/0017328 A1 | 2/2002 | Loo |
| 2002/0029080 A1 | 3/2002 | Mortier et al. |
| 2002/0055711 A1 | 5/2002 | Lavi et al. |
| 2002/0065488 A1 | 5/2002 | Suzuki et al. |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0104584 A1 | 8/2002 | Spero et al. |
| 2002/0115980 A1 | 8/2002 | Niedospial et al. |
| 2002/0121496 A1 | 9/2002 | Thiebault et al. |
| 2002/0123736 A1 | 9/2002 | Fowles et al. |
| 2002/0123737 A1 | 9/2002 | Hart et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0069550 A1 | 4/2003 | Sharp |
| 2003/0073971 A1 | 4/2003 | Saker |
| 2003/0083742 A1 | 5/2003 | Spence et al. |
| 2003/0100866 A1 | 5/2003 | Reynolds |
| 2003/0109846 A1 | 6/2003 | Zinger et al. |
| 2003/0120209 A1 | 6/2003 | Jensen et al. |
| 2003/0135159 A1 | 7/2003 | Daily et al. |
| 2003/0153895 A1 | 8/2003 | Leinsing |
| 2003/0187420 A1 | 10/2003 | Akerlund et al. |
| 2003/0191445 A1* | 10/2003 | Wallen ............... A61M 5/1408 604/411 |
| 2003/0195479 A1 | 10/2003 | Kuracina et al. |
| 2003/0199827 A1 | 10/2003 | Thorne |
| 2003/0199846 A1 | 10/2003 | Fowles et al. |
| 2003/0199847 A1 | 10/2003 | Akerlund et al. |
| 2003/0205843 A1 | 11/2003 | Adams |
| 2003/0236543 A1 | 12/2003 | Brenneman et al. |
| 2004/0010207 A1 | 1/2004 | Flaherty et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0044406 A1 | 3/2004 | Woolfson et al. |
| 2004/0073189 A1 | 4/2004 | Wyatt et al. |
| 2004/0143218 A1 | 7/2004 | Das |
| 2004/0143226 A1 | 7/2004 | Marsden |
| 2004/0153047 A1 | 8/2004 | Blank et al. |
| 2004/0158172 A1 | 8/2004 | Hancock |
| 2004/0162515 A1 | 8/2004 | Chornenky et al. |
| 2004/0162540 A1 | 8/2004 | Walenciak et al. |
| 2004/0167472 A1 | 8/2004 | Howell et al. |
| 2004/0167620 A1 | 8/2004 | Ortiz et al. |
| 2004/0181192 A1 | 9/2004 | Cuppy |
| 2004/0186424 A1 | 9/2004 | Hjertman |
| 2004/0199139 A1 | 10/2004 | Fowles et al. |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0236419 A1 | 11/2004 | Milo |
| 2004/0249341 A1 | 12/2004 | Newbrough et al. |
| 2004/0255952 A1 | 12/2004 | Carlsen et al. |
| 2005/0010287 A1 | 1/2005 | Macoviak et al. |
| 2005/0015070 A1 | 1/2005 | Delnevo et al. |
| 2005/0016626 A1 | 1/2005 | Wilcox et al. |
| 2005/0049553 A1 | 3/2005 | Triplett et al. |
| 2005/0055008 A1 | 3/2005 | Paradis et al. |
| 2005/0070999 A1 | 3/2005 | Spence |
| 2005/0075727 A1 | 4/2005 | Wheatley |
| 2005/0082828 A1 | 4/2005 | Wicks et al. |
| 2005/0124964 A1 | 6/2005 | Niedospial et al. |
| 2005/0137523 A1 | 6/2005 | Wyatt et al. |
| 2005/0137566 A1 | 6/2005 | Fowles et al. |
| 2005/0137702 A1 | 6/2005 | Haug et al. |
| 2005/0148994 A1 | 7/2005 | Leinsing |
| 2005/0159706 A1 | 7/2005 | Wilkinson et al. |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0049209 A1 | 3/2006 | Baker |
| 2006/0058741 A1 | 3/2006 | Gallagher |
| 2006/0074484 A1 | 4/2006 | Huber |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0155257 A1 | 7/2006 | Reynolds |
| 2006/0161192 A1 | 7/2006 | Young |
| 2006/0169348 A1 | 8/2006 | Yigal |
| 2006/0173410 A1 | 8/2006 | Moberg et al. |
| 2006/0178646 A1 | 8/2006 | Harris et al. |
| 2006/0195029 A1 | 8/2006 | Shults et al. |
| 2006/0212004 A1 | 9/2006 | Atil |
| 2006/0224105 A1 | 10/2006 | Thorne et al. |
| 2006/0253084 A1 | 11/2006 | Nordgren |
| 2006/0259004 A1 | 11/2006 | Connell et al. |
| 2006/0259135 A1 | 11/2006 | Navia et al. |
| 2007/0016381 A1 | 1/2007 | Kamath et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0079894 A1 | 4/2007 | Kraus et al. |
| 2007/0083164 A1 | 4/2007 | Barrelle et al. |

(56) References Cited

U.S. PATENT DOCUMENTS

| | | |
|---|---|---|
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0095856 A1 | 5/2007 | Vogel et al. |
| 2007/0106218 A1 | 5/2007 | Yodfat et al. |
| 2007/0106244 A1 | 5/2007 | Mosler et al. |
| 2007/0112324 A1 | 5/2007 | Hamedi-Sangsari |
| 2007/0156112 A1 | 7/2007 | Walsh |
| 2007/0167904 A1 | 7/2007 | Zinger et al. |
| 2007/0167912 A1 | 7/2007 | Causey et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van Manen |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0015496 A1 | 1/2008 | Hamedi-Sangsari |
| 2008/0039935 A1 | 2/2008 | Buch et al. |
| 2008/0077235 A1 | 3/2008 | Kirson |
| 2008/0125860 A1 | 5/2008 | Webler et al. |
| 2008/0135051 A1 | 6/2008 | Lee |
| 2008/0167713 A1 | 7/2008 | Bolling |
| 2008/0172024 A1 | 7/2008 | Yow |
| 2008/0188799 A1 | 8/2008 | Mueller-Beckhaus et al. |
| 2008/0195049 A1 | 8/2008 | Thalmann et al. |
| 2008/0208138 A1 | 8/2008 | Lim et al. |
| 2008/0215015 A1 | 9/2008 | Cindrich et al. |
| 2008/0249473 A1 | 10/2008 | Rutti et al. |
| 2008/0249479 A1 | 10/2008 | Zinger et al. |
| 2008/0249498 A1 | 10/2008 | Fangrow |
| 2008/0262465 A1* | 10/2008 | Zinger ............... A61J 1/1487 604/411 |
| 2008/0262609 A1 | 10/2008 | Gross et al. |
| 2008/0269687 A1 | 10/2008 | Chong et al. |
| 2008/0275407 A1 | 11/2008 | Scheurer |
| 2008/0287905 A1 | 11/2008 | Hiejima et al. |
| 2008/0294100 A1 | 11/2008 | De et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0043253 A1 | 2/2009 | Podaima |
| 2009/0054834 A1 | 2/2009 | Zinger et al. |
| 2009/0054852 A1 | 2/2009 | Takano et al. |
| 2009/0054969 A1 | 2/2009 | Salahieh et al. |
| 2009/0062767 A1 | 3/2009 | Van et al. |
| 2009/0076360 A1 | 3/2009 | Brister et al. |
| 2009/0082750 A1 | 3/2009 | Denenburg et al. |
| 2009/0139724 A1 | 6/2009 | Gray et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216103 A1 | 8/2009 | Brister et al. |
| 2009/0216212 A1 | 8/2009 | Fangrow, Jr. |
| 2009/0257306 A1 | 10/2009 | Coffeen et al. |
| 2009/0267011 A1 | 10/2009 | Hatton et al. |
| 2009/0299325 A1 | 12/2009 | Vedrine et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0042147 A1 | 2/2010 | Janovsky et al. |
| 2010/0049315 A1 | 2/2010 | Kirson |
| 2010/0070027 A1 | 3/2010 | Bonhoeffer et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0137831 A1 | 6/2010 | Tsals |
| 2010/0152658 A1 | 6/2010 | Hanson et al. |
| 2010/0160889 A1 | 6/2010 | Smith et al. |
| 2010/0161047 A1 | 6/2010 | Cabiri |
| 2010/0162548 A1 | 7/2010 | Leidig |
| 2010/0168664 A1 | 7/2010 | Zinger et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger et al. |
| 2010/0204670 A1 | 8/2010 | Kraushaar et al. |
| 2010/0228220 A1 | 9/2010 | Zinger et al. |
| 2010/0241088 A1 | 9/2010 | Ranalletta et al. |
| 2010/0262232 A1 | 10/2010 | Annest |
| 2010/0274184 A1 | 10/2010 | Chun |
| 2010/0274202 A1 | 10/2010 | Hyde et al. |
| 2010/0286661 A1 | 11/2010 | Raday et al. |
| 2010/0305548 A1 | 12/2010 | Kraushaar |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosler et al. |
| 2011/0125056 A1 | 5/2011 | Merchant |
| 2011/0144584 A1 | 6/2011 | Wozencroft |
| 2011/0160655 A1 | 6/2011 | Hanson et al. |
| 2011/0160701 A1 | 6/2011 | Wyatt et al. |
| 2011/0172636 A1 | 7/2011 | Aasmul |
| 2011/0175347 A1 | 7/2011 | Okiyama |
| 2011/0178493 A1 | 7/2011 | Okiyama |
| 2011/0218511 A1 | 9/2011 | Yokoyama |
| 2011/0224640 A1 | 9/2011 | Kuehn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0275988 A1 | 11/2011 | Davis et al. |
| 2011/0276007 A1 | 11/2011 | Denenburg |
| 2011/0319827 A1 | 12/2011 | Leinsing et al. |
| 2012/0022344 A1 | 1/2012 | Kube |
| 2012/0022469 A1 | 1/2012 | Alpert |
| 2012/0053555 A1 | 3/2012 | Ariagno et al. |
| 2012/0059332 A1 | 3/2012 | Woehr et al. |
| 2012/0059346 A1 | 3/2012 | Sheppard et al. |
| 2012/0067429 A1 | 3/2012 | Mosier et al. |
| 2012/0071819 A1 | 3/2012 | Brueggemann et al. |
| 2012/0078214 A1 | 3/2012 | Finke et al. |
| 2012/0123382 A1 | 5/2012 | Kubo |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev et al. |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1 | 12/2012 | Lev et al. |
| 2012/0323187 A1 | 12/2012 | Iwase et al. |
| 2012/0323210 A1 | 12/2012 | Lev et al. |
| 2013/0046269 A1 | 2/2013 | Lev et al. |
| 2013/0053814 A1 | 2/2013 | Mueller-Beckhaus et al. |
| 2013/0096493 A1 | 4/2013 | Kubo et al. |
| 2013/0110049 A1 | 5/2013 | Cronenberg et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Deneburg et al. |
| 2013/0253448 A1 | 9/2013 | Baron et al. |
| 2013/0289530 A1 | 10/2013 | Wyatt et al. |
| 2013/0315026 A1 | 11/2013 | Cheio De Oliveira et al. |
| 2013/0317472 A1 | 11/2013 | Finke |
| 2014/0020793 A1 | 1/2014 | Denenburg et al. |

(56) References Cited

U.S. PATENT DOCUMENTS

| | | | |
|---|---|---|---|
| 2014/0096862 A1 | 4/2014 | Aneas | |
| 2014/0102552 A1* | 4/2014 | Shemesh | A61J 1/1475 |
| | | | 137/315.01 |
| 2014/0150911 A1* | 6/2014 | Hanner | A61M 5/1407 |
| | | | 137/798 |
| 2014/0194854 A1 | 7/2014 | Tsais | |
| 2014/0221940 A1 | 8/2014 | Clauson et al. | |
| 2014/0276215 A1 | 9/2014 | Nelson et al. | |
| 2014/0277052 A1 | 9/2014 | Haselby et al. | |
| 2014/0352845 A1 | 12/2014 | Lev et al. | |
| 2015/0082746 A1 | 3/2015 | Ivosevic et al. | |
| 2015/0088078 A1 | 3/2015 | Lev et al. | |
| 2015/0112297 A1 | 4/2015 | Lev et al. | |
| 2015/0209230 A1 | 7/2015 | Lev et al. | |
| 2015/0250681 A1 | 9/2015 | Lev et al. | |
| 2015/0290390 A1 | 10/2015 | Ring et al. | |
| 2015/0297839 A1 | 10/2015 | Sanders et al. | |
| 2015/0297880 A1 | 10/2015 | Ogawa et al. | |
| 2015/0305770 A1 | 10/2015 | Fill et al. | |
| 2016/0081308 A1 | 3/2016 | Cary et al. | |
| 2016/0081878 A1 | 3/2016 | Marks et al. | |
| 2016/0088995 A1 | 3/2016 | Ueda et al. | |
| 2016/0166824 A1 | 6/2016 | Lev et al. | |
| 2016/0199569 A1* | 7/2016 | Yevmenenko | A61M 5/1412 |
| | | | 604/533 |
| 2016/0228644 A1 | 8/2016 | Cabiri | |
| 2016/0287475 A1 | 10/2016 | Yevmenenko et al. | |
| 2016/0367439 A1 | 12/2016 | Davis et al. | |
| 2018/0008513 A1 | 1/2018 | Iibuchi et al. | |
| 2018/0161243 A1 | 6/2018 | Ariagno | |
| 2018/0221572 A1 | 8/2018 | Schlitt et al. | |
| 2018/0303720 A1 | 10/2018 | Kennard et al. | |
| 2019/0083357 A1 | 3/2019 | David et al. | |
| 2019/0117514 A1 | 4/2019 | Denenburg et al. | |
| 2019/0133885 A1 | 5/2019 | Wu et al. | |
| 2019/0343725 A1 | 11/2019 | Denenburg | |
| 2020/0093692 A1 | 3/2020 | Lev et al. | |
| 2020/0276084 A1 | 9/2020 | Denenburg | |
| 2020/0282133 A1 | 9/2020 | Mason et al. | |
| 2020/0330326 A1 | 10/2020 | Merchant et al. | |
| 2020/0376194 A1 | 12/2020 | Fabrikant et al. | |

FOREIGN PATENT DOCUMENTS

| | | |
|---|---|---|
| CN | 1747683 A | 3/2006 |
| CN | 1863566 A | 11/2006 |
| CN | 1950049 A | 4/2007 |
| CN | 101001661 A | 7/2007 |
| CN | 101687083 A | 3/2010 |
| CN | 201330626512 | 12/2013 |
| CN | 106413799 A | 2/2017 |
| CN | 306375580 S | 3/2021 |
| DE | 1064693 B | 9/1959 |
| DE | 1913926 A1 | 9/1970 |
| DE | 4122476 A1 | 1/1993 |
| DE | 4314657 A1 | 11/1994 |
| DE | 4408498 A1 | 5/1995 |
| DE | 19504413 A1 | 8/1996 |
| DE | 202004012714 U1 | 11/2004 |
| DE | 102007046951 B3 | 2/2009 |
| DE | 202009011019 U1 | 12/2010 |
| EM | 001126270-0001 | 4/2009 |
| EM | 001680703 | 3/2010 |
| EM | 001680703-0002 | 8/2010 |
| EM | 002446062-0002 | 8/2010 |
| EM | 000627237-0001 | 10/2010 |
| EM | 002446062 | 4/2014 |
| EM | 006630893 | 7/2019 |
| EM | 008039507-0004 | 1/2021 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0426403 A1 | 5/1991 |
| EP | 0282545 B1 | 2/1992 |
| EP | 0518397 A1 | 12/1992 |
| EP | 0521460 A1 | 1/1993 |
| EP | 0582038 A2 | 2/1994 |
| EP | 0598918 A1 | 6/1994 |
| EP | 0637443 A1 | 2/1995 |
| EP | 0737467 A1 | 10/1996 |
| EP | 0761562 A1 | 3/1997 |
| EP | 0765652 A1 | 4/1997 |
| EP | 0765853 A1 | 4/1997 |
| EP | 0806597 A1 | 11/1997 |
| EP | 0814866 A1 | 1/1998 |
| EP | 0829248 A2 | 3/1998 |
| EP | 0856331 A2 | 8/1998 |
| EP | 0882441 A2 | 12/1998 |
| EP | 0887085 A2 | 12/1998 |
| EP | 0887885 A2 | 12/1998 |
| EP | 0897708 A2 | 2/1999 |
| EP | 0898951 A2 | 3/1999 |
| EP | 0960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| EP | 2416739 B1 | 6/2016 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 171662 | 10/2005 |
| IL | 186290 | 1/2008 |
| JP | 03-062426 B2 | 9/1991 |
| JP | 03-205560 A | 9/1991 |
| JP | 04-329954 A | 11/1992 |
| JP | 06-050656 U | 7/1994 |
| JP | 08-000710 A | 1/1996 |
| JP | 09-104460 A | 4/1997 |
| JP | 09-104461 A | 4/1997 |
| JP | 10-118158 A | 5/1998 |
| JP | 10-504736 A | 5/1998 |
| JP | 11-503627 A | 3/1999 |
| JP | 11-319031 A | 11/1999 |
| JP | 2000-508934 A | 7/2000 |
| JP | 2000-237278 A | 9/2000 |
| JP | 2000-262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2003-513709 A | 4/2003 |
| JP | 2004-501721 A | 1/2004 |
| JP | 2004-097253 A | 4/2004 |
| JP | 2004-522541 A | 7/2004 |
| JP | 2004-267776 A | 9/2004 |
| JP | 2005-270629 A | 10/2005 |
| JP | 2005537048 A | 12/2005 |
| JP | 2006-061421 A | 3/2006 |
| JP | 2008-220961 A | 9/2008 |
| JP | 2009-513294 A | 4/2009 |
| JP | 4329954 B2 | 9/2009 |
| JP | 2010-063622 A | 3/2010 |

(56) References Cited

FOREIGN PATENT DOCUMENTS

| | | |
|---|---|---|
| JP | 2010-179128 A | 8/2010 |
| JP | 2012-205769 A | 10/2012 |
| JP | 2013-520272 A | 6/2013 |
| JP | 2014-000220 A | 1/2014 |
| JP | 2015-211763 A | 11/2015 |
| JP | 0201915749 | 7/2019 |
| WO | 86/01487 A1 | 3/1986 |
| WO | 86/01712 A1 | 3/1986 |
| WO | 86/05683 A1 | 10/1986 |
| WO | 90/03536 A1 | 4/1990 |
| WO | 94/03373 A1 | 2/1994 |
| WO | 95/07066 A1 | 3/1995 |
| WO | 9507720 A1 | 3/1995 |
| WO | 9513785 A1 | 5/1995 |
| WO | 96/00053 A1 | 1/1996 |
| WO | 96/09083 A1 | 3/1996 |
| WO | 96/29113 A1 | 9/1996 |
| WO | 97/36636 A1 | 10/1997 |
| WO | 98/32411 A1 | 7/1998 |
| WO | 98/37854 A1 | 9/1998 |
| WO | 99/61093 A1 | 12/1999 |
| WO | 01/02490 A1 | 1/2001 |
| WO | 01/28490 A1 | 4/2001 |
| WO | 01/30425 A1 | 5/2001 |
| WO | 01/32524 A1 | 5/2001 |
| WO | 01/60311 A1 | 8/2001 |
| WO | 01/89607 A2 | 11/2001 |
| WO | 01/91693 A2 | 12/2001 |
| WO | 02/02165 A2 | 1/2002 |
| WO | 02/09797 A1 | 2/2002 |
| WO | 02/32372 A1 | 4/2002 |
| WO | 02/36191 A2 | 5/2002 |
| WO | 02/66100 A2 | 8/2002 |
| WO | 02/89900 A1 | 11/2002 |
| WO | 03/51423 A2 | 6/2003 |
| WO | 03/70147 A2 | 8/2003 |
| WO | 03079956 A1 | 10/2003 |
| WO | 2004004806 A1 | 1/2004 |
| WO | 2004/041148 A1 | 5/2004 |
| WO | 2004/096113 A2 | 11/2004 |
| WO | 2005/002492 A1 | 1/2005 |
| WO | 2005/018703 A2 | 3/2005 |
| WO | 2005/041846 A2 | 5/2005 |
| WO | 2005/105014 A2 | 11/2005 |
| WO | 2005120431 A1 | 12/2005 |
| WO | 2006/099441 A2 | 9/2006 |
| WO | 2006/124634 A1 | 11/2006 |
| WO | 2007/015233 A1 | 2/2007 |
| WO | 2007/017868 A1 | 2/2007 |
| WO | 2007052252 A1 | 5/2007 |
| WO | 2007/079305 A2 | 7/2007 |
| WO | 2007/101772 A1 | 9/2007 |
| WO | 2007/105221 A1 | 9/2007 |
| WO | 2007/130809 A2 | 11/2007 |
| WO | 2008/068756 A2 | 6/2008 |
| WO | 2008/076459 A1 | 6/2008 |
| WO | 2008081424 A2 | 7/2008 |
| WO | 2008/126090 A1 | 10/2008 |
| WO | 2008/135989 A1 | 11/2008 |
| WO | 2009/026443 A2 | 2/2009 |
| WO | 2009/029010 A1 | 3/2009 |
| WO | 2009/038860 A2 | 3/2009 |
| WO | 2009/040804 A2 | 4/2009 |
| WO | 2009/087572 A1 | 7/2009 |
| WO | 2009/093249 A1 | 7/2009 |
| WO | 2009/112489 A1 | 9/2009 |
| WO | 2009140511 A1 | 11/2009 |
| WO | 2009/146088 A1 | 12/2009 |
| WO | 2010061743 A1 | 6/2010 |
| WO | 2010/078227 A1 | 7/2010 |
| WO | 2010/117471 A2 | 10/2010 |
| WO | 2010/117580 A1 | 10/2010 |
| WO | 2011/004360 A1 | 1/2011 |
| WO | 2011/024725 A1 | 3/2011 |
| WO | 2011025719 A1 | 3/2011 |
| WO | 2011/039747 A1 | 4/2011 |
| WO | 2011/058545 A1 | 5/2011 |
| WO | 2011/058548 A1 | 5/2011 |
| WO | 2011/077434 A1 | 6/2011 |
| WO | 2011/090955 A1 | 7/2011 |
| WO | 2011/104711 A1 | 9/2011 |
| WO | 2011/132657 A1 | 10/2011 |
| WO | 2011/156373 A1 | 12/2011 |
| WO | 2011150037 A1 | 12/2011 |
| WO | 2012/004784 A1 | 1/2012 |
| WO | 2012/004790 A2 | 1/2012 |
| WO | 2012/063230 A1 | 5/2012 |
| WO | 2012/143921 A1 | 10/2012 |
| WO | 2012/150587 A1 | 11/2012 |
| WO | 2013/001525 A1 | 1/2013 |
| WO | 2013/127813 A1 | 9/2013 |
| WO | 2013/134246 A1 | 9/2013 |
| WO | 2013/148435 A1 | 10/2013 |
| WO | 2013/156944 A1 | 10/2013 |
| WO | 2013/156994 A1 | 10/2013 |
| WO | 2014/033706 A2 | 3/2014 |
| WO | 2014/033710 A1 | 3/2014 |
| WO | 2014/099395 A1 | 6/2014 |
| WO | 2014/170888 A1 | 10/2014 |
| WO | 2014/174278 A1 | 10/2014 |
| WO | 2015009746 A2 | 1/2015 |
| WO | 2015019343 A1 | 2/2015 |
| WO | 2016/023590 A1 | 2/2016 |
| WO | 2017/203512 A1 | 11/2017 |
| WO | 2018/104932 A1 | 6/2018 |
| WO | 2018104930 A1 | 6/2018 |
| WO | 2018178971 A1 | 10/2018 |
| WO | 2020/222220 A1 | 11/2020 |

OTHER PUBLICATIONS

Int'l Search Report and Written Opinion dated Jul. 21, 2020 in Int'l Application No. PCT/IL2020/050362.
Int'l Search Report and Written Opinion dated Mar. 29, 2019 in Int'l Application No. PCT/IB2018/059577.
Int'l Search Report and Written Opinion dated May 4, 2011 in Int'l Application No. PCT/IL2010/001077.
Int'l Search Report dated Apr. 24, 2020 in Int'l Application No. PCT/US2020/050020.
Int'l Search Report dated Aug. 25, 2008 in Int'l Application No. PCT/IL2008/000517.
Int'l Search Report dated Jan. 22, 2013 in Int'l Application No. PCT/IL2012/000354.
Int'l Search Report dated Nov. 20, 2006 in Int'l Application No. PCT/IL2006/000881.
International Search Report and Written Opinion dated Oct. 17, 2014 in International Application No. PCT/IL2014/050680.
International Search Report dated Jan. 23, 2007 in Int'l Application No. PCT/IL/2006/001228.
International Search Report dated Mar. 30, 2011 in Int'l Application No. PCT/IL2010/000939.
International Search Report dated Aug. 28, 2008 in Int'l Application No. PCT/IL2008/000606.
Intl Search Report dated Dec. 6, 2006 in Int'l Application No. PCT/IL2006/000912.
IV disposables sets catalogue, Cardinal Health, Alaris(Registered) products, SmartSite(Registered) access devices and accessories product No. 10013365, SmartSite add-0n bag access device with spike adapter and needle-free valve bag access port, pp. 1-5, Fall edition (2007).
Kipp, "Plastic Material Data Sheets," retrieved from the Internet: http://www.knovel.com/web/portal/browse/display?_EXT_KNOVEL_DISPLAY_bookid=1023&VerticalID=0, retrieved on Feb. 9, 2011.
MixJect, downloaded from webpage: http://www.westpharma.com/en/products/Pages/MixjecLaspx, Download Date Aug. 8, 2012, 1 page.
MixJet Product Information Sheet, downloaded from webpage: http://www.westpharma.com/SiteCollectionDocuments/Recon/mixject%20product%20sheet.pdf; 1 page.

(56) References Cited

OTHER PUBLICATIONS

Non-Vented Vial Access Pin with ULTRASITE.RM. Valve, B. Braun Medical, Inc. website and product description, 3 pages, Feb. 2006.
Notice of Allowance dated Jan. 12, 2016 in U.S. Appl. No. 14/385,212 by Lev.
Notice of Allowance dated Mar. 17, 2016 in U.S. Appl. No. 29/502,037 by Lev.
Novel Transfer, Mixing and Drug Delivery System, MOP Medimop Medical Projects Ltd. Catalog, 4 pages, Rev. 4, 2004.
Office Action dated Apr. 17, 2014 in CN Application No. 201080051201.4.
Office Action dated Apr. 2, 2013 in U.S. Appl. No. 13/505,790.
Office Action dated Apr. 20, 2010 in U.S. Appl. No. 11/997,569.
Office Action dated Apr. 9, 2015 in U.S. Appl. No. 13/883,289 by Lev.
Office Action dated Aug. 20, 2013 in U.S. Appl. No. 13/576,461 by Lev.
Office Action dated Aug. 24, 2015 in U.S. Appl. No. 14/366,306 by Lev.
Office Action dated Aug. 3, 2011 in JP Application No. 2008-525719.
Office Action dated Aug. 7, 2015 in JP Application No. 2015-529206.
Office Action dated Dec. 13, 2010 in U.S. Appl. No. 12/293,122.
Office Action dated Dec. 20, 2010 in U.S. Appl. No. 12/063,176.
Office Action dated Dec. 23, 2010 in U.S. Appl. No. 29/334,696.
Office Action dated Dec. 9, 2015 in U.S. Appl. No. 29/478,723 by Lev.
Office Action dated Dec. 9, 2015 in U.S. Appl. No. 29/478,726 by Lev.
Office Action dated Feb. 13, 2014 in U.S. Appl. No. 13/884,981 by Denenburg.
Office Action dated Feb. 20, 2009 in U.S. Appl. No. 11/694,297.
Office Action dated Feb. 22, 2005 in U.S. Appl. No. 10/062,796.
Office Action dated Feb. 7, 2011 in U.S. Appl. No. 12/783,194.
Office Action dated Jan. 17, 2014 in CN Application No. 201180006534.X.
Office Action dated Jan. 2, 2014 in U.S. Appl. No. 13/505,881 by Lev.
Office Action dated Jan. 2, 2015 in U.S. Appl. No. 29/438,141 by Gilboa.
Office Action dated Jan. 20, 2010 in JP Application No. 2007-510229.
Office Action dated Jan. 23, 2013 in U.S. Appl. No. 12/112,490 by Zinger.
Office Action dated Jan. 5, 2015 in U.S. Appl. No. 29/413,220 by Lev.
Office Action dated Jul. 11, 2011 in U.S. Appl. No. 12/293,122.
Office Action dated Jul. 13, 2012 in U.S. Appl. No. 12/112,490 by Zinger.
Office Action dated Jul. 31, 2014 in U.S. Appl. No. 29/438,141 by Gilboa.
Office Action dated Jun. 1, 2010 in U.S. Appl. No. 11/568,421.
Office Action dated Jun. 14, 2012 in U.S. Appl. No. 29/376,980.
Office Action dated Jun. 15, 2011 in JP Application No. 2008-538492.
Summit International Medical Technologies, Inc., Vial Direct to Bag Spike, 2020.
Merchant "An engineered control device for needle free reconstitution and transfer of compounded sterile intravenous drug solutions for immediate use to assist in complying with United States Pharmacopeia Chapter <797> standard", Adv Care, 2 pages, 2018.
West Vial2Bag DC system, Oct. 2, 2014, https://web.archive.org/web/20140020651331/http://www.westpharma.com/en/products/Pages/Reconstitutionsystems.aspx.
Youtube.com, Vial2Bag DC, Aug. 21, 2014, https://www.youtube.com/watch?v=FEOkglxNBrs.
Article with picture of West Pharmaceutical Services Vial2Bag Needleless System, [on-line]; IPIPS Newsletter, Oct. 26, 2007], [retrieved from Internet Feb. 16, 2010]; URL: ,http://www.isips.org/reports/ISIPS_Newsletter_October_26_2007.html.> (7 pages, see pp. 5-6).
Facebook "West Pharmaceutical Services, Inc.", first available Oct. 21, 2014 (https://www.facebook.com/westpharma/photos/710246859056351)(2014).
Youtube, "vial2Bag DC", first available Feb. 1, 2018, (https://www.youtube.com/watch?v=abSKPo5e_Hg) (Year:2018).
Youtube, "ADVCARE—Vial Direct to bag Spoke", first available Oct. 31, 2018 (https://www.youtube.com/watch?v=dd8ctggkrfM&feature=emb_title)(2018).
Office Action dated Jun. 15, 2012 in U.S. Appl. No. 29/413,170.
Office Action dated Jun. 21, 2012 in U.S. Appl. No. 12/596,167.
Office Action dated Jun. 8, 2010 in U.S. Appl. No. 12/112,490 by Zinger.
Office Action dated Mar. 1, 2012 in CN Application No. 200880108283.4.
Office Action dated Mar. 10, 2015 in EP Application No. 12 812 395.7.
Office Action dated Mar. 13, 2012 in CA Application No. 2,563,643.
Office Action dated Mar. 17, 2015 in U.S. Appl. No. 14/504,979 by Lev.
Office Action dated Mar. 25, 2016 in U.S. Appl. No. 29/478,726 by Lev.
Office Action dated Mar. 28, 2016 in JP Application No. 2016-507113.
Office Action dated Mar. 6, 2012 in U.S. Appl. No. 12/678,928.
Office Action dated May 12, 2011 in U.S. Appl. No. 12/063,176.
Office Action dated May 27, 2010 in U.S. Appl. No. 11/559,152.
Office Action dated May 28, 2015 in U.S. Appl. No. 14/391,792 by Lev.
Office Action dated May 31, 2013 in U.S. Appl. No. 13/505,790.
Office Action dated May 6, 2014 in U.S. Appl. No. 13/505,881 by Lev.
Office Action dated Nov. 11, 2013 in IL Application No. 218730.
Office Action dated Nov. 28, 2013 in IN Application No. 4348/DELNP/2008.
Office Action dated Nov. 29, 2010 in U.S. Appl. No. 11/568,421.
Office Action dated Oct. 5, 2005 in U.S. Appl. No. 10/062,796.
Office Action dated Oct. 5, 2015 in U.S. Appl. No. 14/385,212 by Lev.
Office Action dated Oct. 6, 2003 in U.S. Appl. No. 10/062,796.
Office Action dated Oct. 8, 2013 in CN Application No. 201080043825.1.
Office Action dated Sep. 28, 2010 in U.S. Appl. No. 12/112,490 by Zinger.
Office Action issued Jul. 31, 2012 in U.S. Appl. No. 12/598,469.
Overview—Silicone Rubber [retrieved from http://www.knovel.com/web/portal/browse/display?_EXT_KNOVEL_DISPLAY_bookid=1023&Vertica11D=0 on Feb. 9, 2011].
Photographs of Alaris Medical Systems SmartSite.RTM. device, 5 pages, 2002.
Publication dale of Israeli Patent Application 186290 [on-line]. ]Retrieved from Internet May 24, 2010]. URL:<http://www.ilpatsearch.justice.gov.il/UI/Requestslistaspx>. (1 page).
Smart Site Needle-Free Systems, Alaris Medical Systems Webpage, 4 pages, Feb. 2006.
Smart Site.RTM. Alaris Medical Systems Product Brochure, 4 pages, Issue 1, Oct. 1999.
The MixJect transfer system, as shown in the article, "Advanced Delivery Devices," Drug Delivery Technology Jul./Aug. 2007 vol. 7 No.7 [on-line]. [Retrieved from Internet May 14, 2010.] URL: <http://www.drugdeiverytech-online.com/drugdelivery/200707/?pg=28pg28>. (3 pages).
Translation of Office Action dated Apr. 15, 2013 in JP Application No. 2008-538492.
Translation of Office Action dated Jun. 18, 2012 in JP Application No. 2008-538492.
U.S. Appl. No. 14/005,751 by Denenburg, filed Sep. 17, 2013.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.

(56) References Cited

OTHER PUBLICATIONS

U.S. Appl. No. 13/883,289 by Lev, filed May 3, 2013.
U.S. Appl. No. 13/884,981 by Denenburg, filed May 13, 2013.
U.S. Appl. No. 14/345,094 by Lev, filed Mar. 14, 2014.
U.S. Appl. No. 14/366,306 by Lev, filed Jun. 18, 2014.
U.S. Appl. No. 14/385,212 by Lev, filed Sep. 15, 2014.
U.S. Appl. No. 14/391,792 by Lev, filed Oct. 10, 2014.
U.S. Appl. No. 14/423,595 by Lev, filed Feb. 24, 2015.
U.S. Appl. No. 14/423,612 by Lev, filed Feb. 24, 2015.
U.S. Appl. No. 14/425,582 by Lev, filed Mar. 3, 2015.
U.S. Appl. No. 14/504,979 by Lev, filed Oct. 2, 2014.
U.S. Appl. No. 14/784,300 by Lev, filed Oct. 14, 2015.
U.S. Appl. No. 14/888,590 by Marks, filed Nov. 2, 2015.
U.S. Appl. No. 29/438,134 by Lev, filed Nov. 27, 2012.
Int'l Search Report and Written Opinion dated Mar. 23, 2020 in Int'l Application No. PCT/IL2020/050048.
Decision to Grant dated Apr. 12, 2010 in EP Application No. 08738307.1.
Drug Administration Systems product information sheets; http://www.westpharma.com/eu/en/products/Pages/Vial2Bag.aspx; pp. 1-3 (admitted prior art).
English translation of an Office Action dated Apr. 28, 2014 in JP Application No. 2013-537257.
English translation of an Office Action dated Aug. 28, 2014 in JP Application No. 2013-168885.
English translation of an Office Action dated Dec. 25, 2013 in CN Application No. 201180006530.1.
English translation of an Office Action dated Dec. 4, 2013 in CN Application No. 201080051210.3.
English translation of an Office Action dated Feb. 4, 2014 in JP Application No. 2012-554468.
English translation of an Office Action dated Jan. 9, 2014 in JP Application No. 2010-526421.
English translation of an Office Action dated Jul. 26, 2013 in JP Application No. 2012-538464.
English translation of an Office Action dated Jun. 19, 2013 in JP Application No. 2012-531551.
English translation of an Office Action dated Jun. 30, 2014 in CN Application No. 201180052962.6.
English translation of an Office Action dated Sep. 10, 2013 in JP Application No. 2012-554468.
Extended European Search Report dated Jun. 3, 2014 in EP Application No. 08781828.2.
Grifols Vial Adapter Product Literature, 2 pages, Jan. 2002.
http://www.knovel.com/web/portal/browse/display?.sub.-EXT.sub.-KNOVELsu-b.-DISPLAY.sub.-bookid=1023&VerticalID=0 [retrieved on Feb. 9, 2011].
http://www.westpharma.com/en/products/Pages/Mixject.aspx (admitted prior art), [Retrieved on Aug. 8, 2012].
http://www.westpharma.com/eu/en/products/Pages/Vial2Bag.aspx; Drug Adminsitration Systems product information sheets pp. 1-3.
http://www.westpharma.com/eu/SiteCollectionDocuments/Recon/mixject%20produ-ct%20sheet.pfg: MIXJECT product information sheet pp. 1, Sep. 10, 2010.
Int'l Preliminary Report on Patenability dated Oct. 20, 2009 in Int'l Application No. PCT/IL2008/000517.
Int'l Preliminary Report on Patentability dated Jan. 14, 2014 in Int'l Application No. PCT/IL2012/050516.
Int'l Preliminary Report on Patentability dated May 6, 2008 in Int'l Application No. PCT/IL2006/001228.
Int'l Preliminary Report on Patentability dated May 12, 2014 in Int'l Application No. PCT/IL2013/050316.
Int'l Preliminary Report on Patentability dated Aug. 20, 2014 in Int'l Application No. PCT/IL2012/050407.
Int'l Preliminary Report on Patentability dated Aug. 28, 2012 in Int'l Application No. PCT/IL2011/000186.
Int'l Preliminary Report on Patentability dated Sep. 24, 2013 in Int'l Application No. PCT/IL2012/000354.
Int'l Preliminary Report on Patentability dated Dec. 4, 2007 in Int'l Application No. PCT/IL2006/000912.
Int'l Preliminary Report on Patentability dated Jun. 19, 2006 in Int'l Application No. PCT/IL2005/000376.
Int'l Preliminary Report on Patentability dated Jun. 19, 2008 in Int'l Application No. PCT/IL2007/000343.
Int'l Search Report & Written Opinion dated Mar. 7, 2012 in Int'l Application No. PCT/IL2011/000829.
Int'l Search Report and Written Opinion dated Mar. 6, 2012 in Int'l Application No. PCT/IL2011/000834.
Int'l Search Report and Written Opinion dated May 8, 2014 in Int'l Application No. PCT/IL2013/050706.
Int'l Search Report and Written Opinion dated Jul. 16, 2014 in Int'l Application No. PCT/IL2014/050327.
Int'l Search Report and Written Opinion dated Sep. 2, 2014 in Int'l Application No. PCT/IL2014/050405.
Int'l Search Report dated Feb. 3, 2011 in Int'l Application No. PCT/IL2010/000777; Written Opinion.
Int'l Search Report dated Mar. 17, 2011 in Int'l Application No. PCT/IL2010/000854; Written Opinion.
Int'l Search Report dated Mar. 18, 2013 in Int'l Application No. PCT/IL2012/050516.
Int'l Search Report dated Jun. 5, 2013 in Int'l Application No. PCT/IL2012/050407.
Int'l Search Report dated Jun. 19, 2013 in Int'l Application No. PCT/IL2013/050167.
Int'l Search Report dated Jul. 1, 2013 in Int'l Application No. PCT/IL2013/050180.
Int'l Search Report dated Jul. 26, 2013 in Int'l Application No. PCT/IL2013/050316.
Int'l Search Report dated Jul. 31, 2013 in Int'l Application No. PCT/IL2013/050313.
Int'l Search Report dated Aug. 16, 2012 in Int'l Application No. PCT/IL2012/000164.
Int'l Search Report dated Oct. 17, 2005 in Int'l Application No. PCT/IL2005/000376.
Int'l Search Report dated Oct. 17, 2011 in Int'l Application No. PCT/IL2011/000511.
Int'l Search Report dated Nov. 25, 2010 in Int'l Application No. PCT/IL2010/000530.
Int'l Search Report dated Mar. 12, 2009 in Int'l Application No. PCT/IL2008/001278.
Int'l Search Report dated Mar. 27, 2009 in Int'l Application No. PCT/US2008/070024.
Int'l Search Report dated Jul. 12, 2011 in Int'l Application No. PCT/IL2011/000186.
Int'l Search Report dated Jul. 12, 2011 in Int'l Application No. PCT/IL2011/000187.
Int'l Search Report dated Jul. 27, 2007 in Int'l Application No. PCT/IL2007/000343.
U.S. Appl. No. 29/438,141 by Gilboa, filed Nov. 27, 2012.
U.S. Appl. No. 29/478,723 by Lev, filed Jan. 8, 2014.
U.S. Appl. No. 29/478,726 by Lev, filed Jan. 8, 2014.
U.S. Appl. No. 29/502,037 by Lev, filed Sep. 11, 2014.
U.S. Appl. No. 29/502,053 by Lev, filed Sep. 11, 2014.
U.S. Appl. No. 29/544,969 by Ben Shalom, filed Nov. 9, 2015.
Vial-Mate Adapter Device, Baxter, May 2017, downloaded from web page:http://www.baxtermedicationdeliveryproducts.com/drug-delivery/vialmate.html, Download Date: Jul. 28, 2017, original posting date: unknown, 1 page.
Vial2Bag DC, downloaded from webpage: https://www.youtube.com/watch?v=FEOkg1xNBrs, Original posting date: Aug. 21, 2014, 1 page.
Voutube.com, Vial2Bag DC, Aug. 21, 2014, https://www.youtube.com/watch?v=FEOkglxNBrs.
Written Opinion dated Aug. 16, 2012 in Int'l Application No. PCT/IL2012/000164.
Written Opinion dated Jul. 31, 2013 in Int'l Application No. PCT/IL2013/050313.
Written Opinion dated Jun. 5, 2013 in Int'l Application No. PCT/IL2012/050407.
Written Opinion of ISR dated Jun. 19, 2006 in Int'l Application No. PCT/IL2005/000376.
Written Opinion of the Int'l Searching Authority dated Oct. 27, 2008 in Int'l Application No. PCT/US2008/070024.

(56) References Cited

OTHER PUBLICATIONS

Written Opinion of the ISR dated Oct. 17, 2009 in Int'l Application No. PCT/IL08/00517.
Youtube, "Vial2Bag.RTM. Needleless IV Transfer System from Helapet Ltd", first available Aug. 21, 2014 (https://www.youtube.com/watch?v=yFejsv0eemE) (Year: 2014).
Office Action dated May 25, 2021 issued in Japanese Application No. 2020-553506.
Author unknown, Progressive Medical inc. is proud to announce the launch of West's VIAL2BAG Agvanced, Progressive Medinc ., [Post Date Oct. 23, 2020], [Site seen Jan. 25, 2022], Seen at URL: https://www.progressivemedinc.com/west-launches-vial2bag-advanced-20mm-admixture-device/ (Year: 2020).
Our Vial2Bag Advanced™ 20mm admixture device , West Pharma, WestPharma @twitter, [Postdate Mar. 19, 021], [Siteseen Jan. 25, 2022], Seen at URL: https://twitter.eom/westpharma/status/137292105//66739971 (Year: 2021).

* cited by examiner

LIQUID TRANSFER DEVICE WITH DUAL LUMEN IV SPIKE

CROSS REFERENCE TO RELATED APPLICATIONS

This application is a Section 371 of International Application No. PCT/IL20/50048, filed Jan. 13, 2020, and claims priority and benefit from U.S. Provisional Patent Application No. 62/840,620, titled "Liquid Transfer Device With Lumen IV Spike", filed on Apr. 30, 2019, the entire contents of which are incorporated by reference herein.

BACKGROUND OF THE DISCLOSURE

The present disclosure is generally directed to liquid transfer devices.

Conventional infusion liquid containers containing an infusion liquid to be delivered to a patient generally take the form of an infusion liquid bag, an infusion liquid bottle, and the like. A pre-filled syringe or vial is generally utilized to add a high concentration of a drug to the infusion liquid contents, via a liquid transfer device, to form a diluted, medicated infusion liquid. Thereafter, an infusion set including an IV spike may be inserted into an IV port of the liquid transfer device for infusion of medicated infusion liquid contents to a patient. Minimizing the risk of a patient receiving a portion of the drug in a highly concentrated, undiluted form is important for patient safety.

BRIEF SUMMARY OF THE DISCLOSURE

The present disclosure realizes the advantageous manufacture of a liquid transfer device having separate lumens: one for mixing the high concentration of drug with the infusion liquid, and one for transferring the diluted, medicated infusion liquid to the infusion set, as an added measure to prevent the patient from receiving a portion of the drug in an undiluted, high concentration form. The present disclosure additionally or alternatively realizes the advantageous manufacture of a liquid transfer device capable of mixing the fluid within the lumen between the IV port and the port connected to the medicated infusion liquid contents prior to administering the medicated infusion liquid contents to a patient.

Briefly stated, one aspect of the present disclosure is directed to a liquid transfer device configured for use with each of an infusion liquid container containing an infusion liquid and having an intravenous (IV) port for administering the infusion liquid, a vial containing a medicament additive sealed by a vial stopper, and an infusion set including an IV spike for sealing insertion into an IV port and a connector, such as an infusion set, for administration purposes to a patient. The liquid transfer device includes a monolithic trifurcated connector body defining a barrel at a first end thereof, a single IV spike at a second end thereof and a vial adapter lumen at a third end thereof. An IV port is connected to the barrel and configured to sealingly receive the IV spike of the infusion set. A vial adapter is permanently secured to the vial adapter lumen and configured to telescopically mount onto the vial. The vial adapter includes a vial spike fluidly connected with the vial adapter lumen and configured to puncture the vial stopper upon mounting of the vial adapter onto the vial for flow communication therewith. The single IV spike is configured to sealingly insert into the IV port of the infusion liquid container. The single IV spike has a first IV spike lumen fluidly connected at a proximal end thereof with only the vial adapter lumen via the trifurcated connector body and a second IV spike lumen fluidly connected at a proximal end thereof with only the IV port via the trifurcated connector body, thereby separating fluid communication between the vial adapter and the single IV spike from fluid communication between the IV port and the single IV spike while enabling initial introduction of the medicament additive from the vial to the infusion liquid container through the vial adapter and the first IV spike lumen for mixing with the infusion liquid to form a medicated infusion liquid, and enabling subsequent administration of the medicated infusion liquid to a patient from the infusion liquid container through the second IV spike lumen and the IV port to the infusion set. The first IV spike lumen has a first peripherally disposed distal aperture and the second IV spike lumen has a second peripherally disposed distal aperture.

Briefly stated, another aspect of the present disclosure is directed to a method of using a liquid transfer device having a monolithic trifurcated connector body defining a barrel at a first end thereof, a single intravenous (IV) spike at a second end thereof and a vial adapter lumen at a third end thereof. The method includes the steps of mounting a vial adapter permanently secured to the vial adapter lumen onto a vial containing a medicament additive, and, in turn, piercing a stopper of the vial with a vial spike of the vial adapter fluidly connected with the vial adapter lumen; piercing an IV port of an infusion liquid container containing an infusion liquid with the single IV spike; and adding the medicament additive within the vial to the infusion liquid within the infusion liquid container (i.e. mixing the medicament with the infusion liquid) to obtain a medicated infusion liquid via the vial adapter lumen and a first IV spike lumen of the single IV spike. The first IV spike lumen is fluidly connected at a proximal end thereof with only the vial adapter lumen via the trifurcated connector body and has a first peripherally disposed distal aperture proximate a distal end of the single IV spike. The method also includes the step of inserting an IV spike of an infusion set into an IV port of the liquid transfer device, the IV port of the liquid transfer device being fluidly connected to a second IV spike lumen of the single IV spike. The second IV spike lumen is fluidly connected at a proximal end thereof with only the IV port and has a second peripherally disposed distal aperture proximate the distal end of the single IV spike, thereby fluidly connecting the infusion set with the infusion liquid container for administration of the medicated infusion liquid to a patient.

BRIEF DESCRIPTION OF THE DRAWINGS

The following detailed description of aspects of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1A:
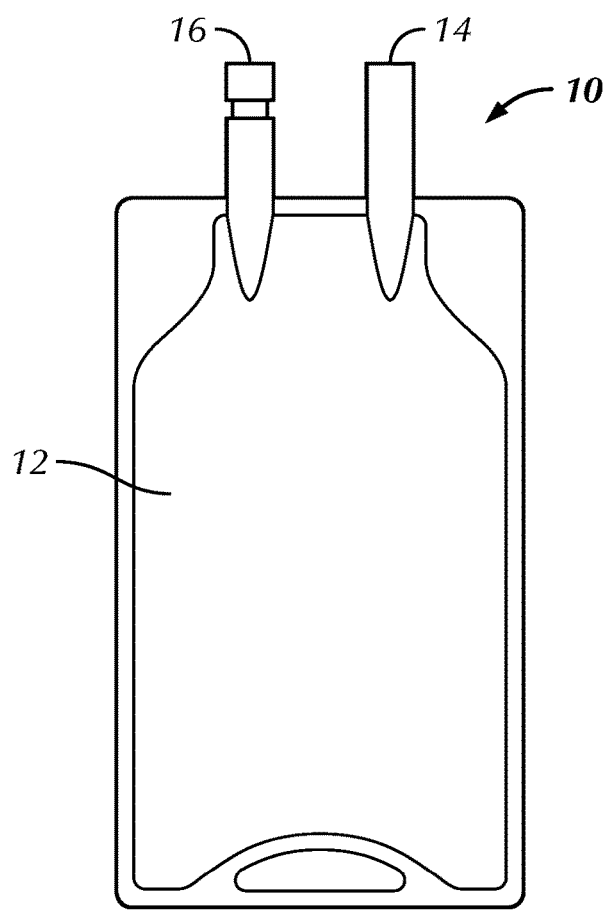
FIG. 1A is a front elevational view of an infusion liquid container in the form of a bag usable with a liquid transfer device according to the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the liquid transfer device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1B:
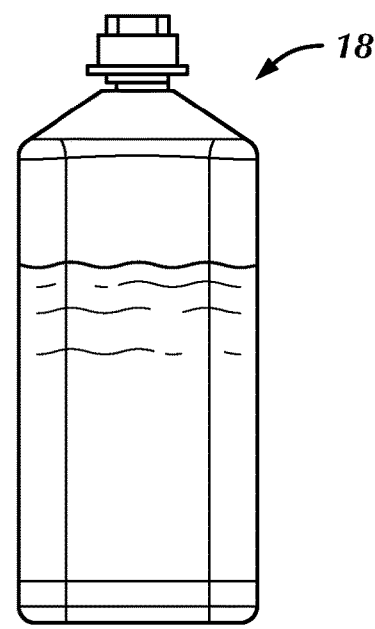
FIG. 1B is a front elevational view of an infusion liquid container in the form of a flexible bottle usable with a liquid transfer device according to the present disclosure.
Figure 1C:
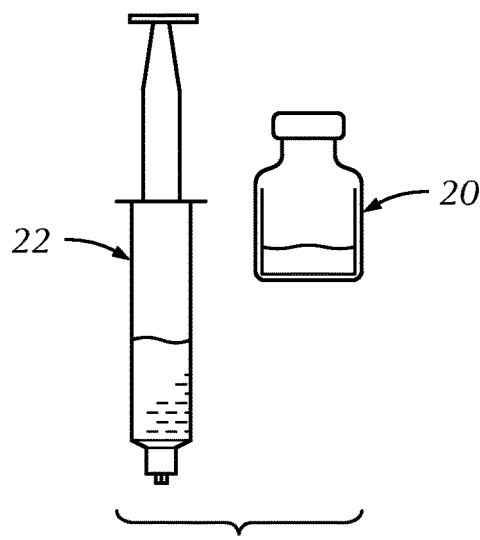
FIG. 1C is a front elevational view of a pre-filled needleless syringe and a vial usable with the liquid transfer device according to the present disclosure.

Referring to the drawings in detail, wherein like numerals indicate like elements throughout, there is shown in FIGS. 2A-6 a liquid transfer device 30, in accordance with a first embodiment of the present disclosure, intended for use with the combination of infusion liquid containers containing an infusion liquid and additive transfer devices. In the illustrated embodiment, the liquid transfer device 30 is intended for use with an infusion liquid container in the form of an infusion liquid bag 10 (FIG. 1A). As should be understood by those of ordinary skill in the art, a conventional infusion liquid bag 10 includes a reservoir 12 containing infusion liquid, in fluid communication with an intravenous administration port 14 and an additive port 16. The infusion liquid bag 10 is collapsible upon administration of the infusion liquid therefrom. The liquid transfer device 30 may also be used with an infusion liquid container in the form of a flexible infusion liquid bottle 18 (FIG. 1B) or the like. The liquid transfer device 30 of the illustrated embodiment is also intended for use with an additive transfer device in the form of a sealed vial 20 (FIG. 1C). The vial 20 generally contains a highly concentrated medicament liquid additive or a lyophilized powder drug requiring reconstitution prior to administration to a patient, i.e., requiring mixing with the infusion liquid in the bag 10 to form a medicated infusion liquid administered to a patient. The contents of the vial 20 are, therefore, introduced into the infusion liquid bag 10 via the liquid transfer device 30 (as will be described in further detail below). The liquid transfer device 30 may also, however, take a different configuration intended for use with a syringe 22 (FIG. 1C) containing a medicament liquid additive.

The liquid transfer device 30 includes a trifurcated connector body 32. In the illustrated embodiment of FIGS. 2A-6, the trifurcated connector body 32 is a monolithic body defining a barrel 34 at a first end thereof, a single IV spike 36 at a second end thereof, and a vial adapter 38 at a third end thereof, but the disclosure is not so limited (as described further below). As shown best in FIGS. 2B, 4B and 5, the barrel 34 defines an internal chamber 34a having an open proximal end 34b for slidably receiving a plunger 40 (as will be described further below). The IV spike 36 defining the second end of the trifurcated body 32 enables use of the liquid transfer device 30 with infusion liquid bags 10, i.e., for sealingly inserting the IV spike 36 into the administration port 14 of the bag 10. The IV spike 36 may be constructed from a suitable rigid metal, polymeric or plastic material, such as, for example, polycarbonate and the like. A flange 33 extends laterally from the IV spike 36 proximate a proximal end thereof to provide a gripping or bearing surface to enable a user to more easily insert the IV spike 36 into a liquid container, such as bag 10. The IV spike may optionally include a feature, such as raised step 35 around the circumferential surface of the IV spike 36, for restricting insertion depth into the administration port 14 of the bag 10. In one embodiment, the flange 33 may also be formed as an injection molded monolithic structure with the connector body 32, but the disclosure is not so limited. A spike cap (not shown) may removably cover the IV spike 36 when not in use.

As shown, the IV spike 36 is co-directional and/or coaxial with the barrel 34 and includes two internal lumens 36a, 36b. In the illustrated configurations, the lumens 36a, 36b extend generally parallel to one another. The first IV spike lumen 36a is continuously and directly fluidly connected at a proximal end with only a vial adapter lumen 37 located within the vial adapter 38 angularly bifurcating from, i.e., branching off of, the IV spike 36. The first IV spike lumen 36a includes a first peripherally disposed distal aperture 36c. As shown best in FIGS. 2B, 4B and 5, the first IV spike lumen 36a is not fluidly connected at the proximal end thereof with the barrel chamber 34a. The second IV spike lumen 36b is directly fluidly connectable at a proximal end with only the barrel chamber 34a and includes a second peripherally disposed distal aperture 36d, separate from the first distal aperture 36c of the first IV spike lumen 36a. The second IV spike lumen 36b is not fluidly connected at the proximal end thereof with the vial adapter lumen 37 or at any point along the length of the IV spike 36. In other words, IV spike 36 includes two separate lumens 36a, 36b that extend through the IV spike 36 to provide discrete fluid paths that are not connected within the IV spike 36. Thus, fluid communication between the vial adapter 38 and the IV spike 36 is separate from fluid communication between the barrel chamber 34a and the IV spike 36.

The vial adapter 38 is configured to mount onto a vial 20 to enable usage of the device 30 with an additive transfer device in the form of a vial 20. In one configuration, the vial adapter 38 may be integrally formed at the third end of the connector body 32, i.e., monolithically formed with the terminal end of the vial adapter lumen 37 or otherwise permanently secured and sealed to the terminal end of the vial adapter lumen 37, but the disclosure is not so limited. As used herein through the specification and the claims, "permanently secured" means not disconnectable/removable without causing damage to the device or portion thereof. As one non-limiting example, the vial adapter 38 may be ultrasonically welded to the vial adapter lumen 37.

Figure 7A:
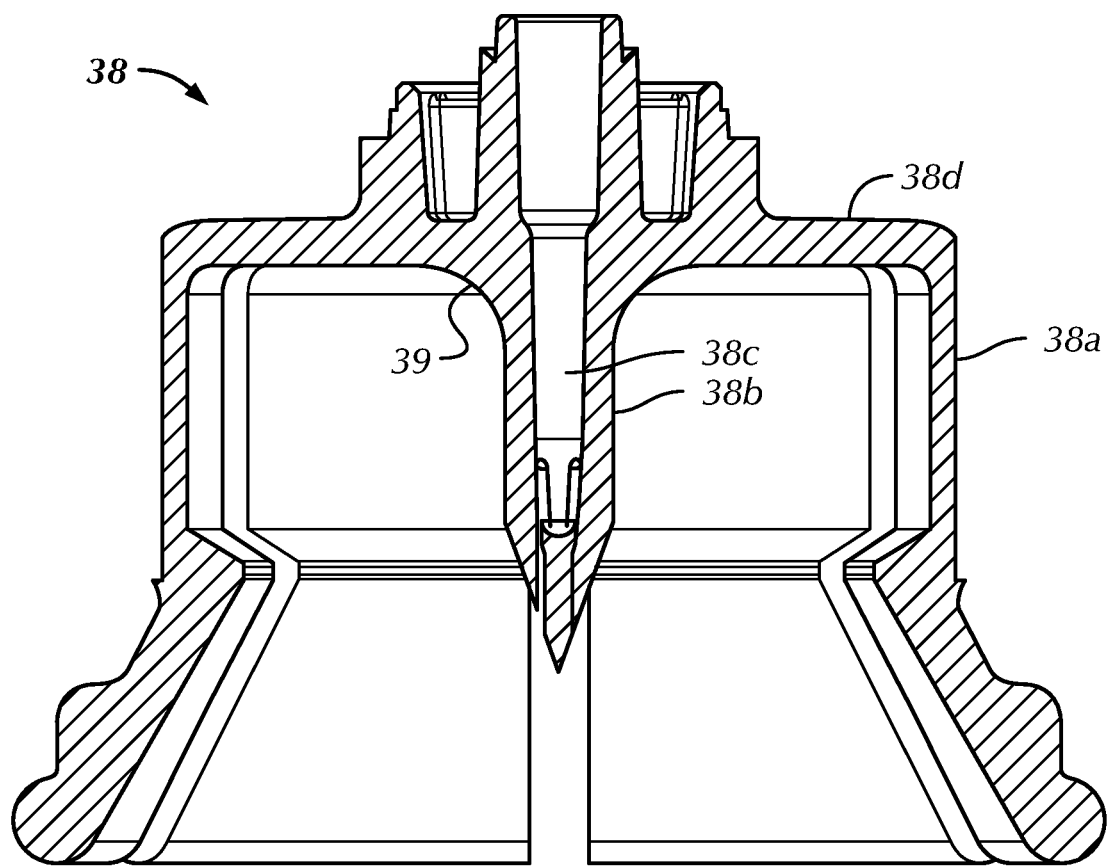
FIG. 7A is an enlarged cross-sectional elevational view of one configuration of a vial adapter of the liquid transfer device of FIG. 2A.

Referring to FIG. 7A, the vial adapter 38 includes a top wall 38d, a flexible and/or flared skirt 38a depending therefrom for telescopic snap fit mounting onto a vial 20 (in a standard manner) and a vial spike 38b for puncturing the vial 20, e.g., through a stopper thereof, to fluidly communicate with the interior of the vial 20. The puncturing vial spike 38b includes a lumen 38c in fluid communication with the vial adapter lumen 37, and, in turn with the first IV spike lumen 36a. As should be understood by those of ordinary skill in the art, the inner diameter of the vial spike 38b, i.e., the diameter of the lumen 38c, and/or the outer diameter of the vial spike 38b may be dimensioned as appropriate for the intended use.

Figure 7B:
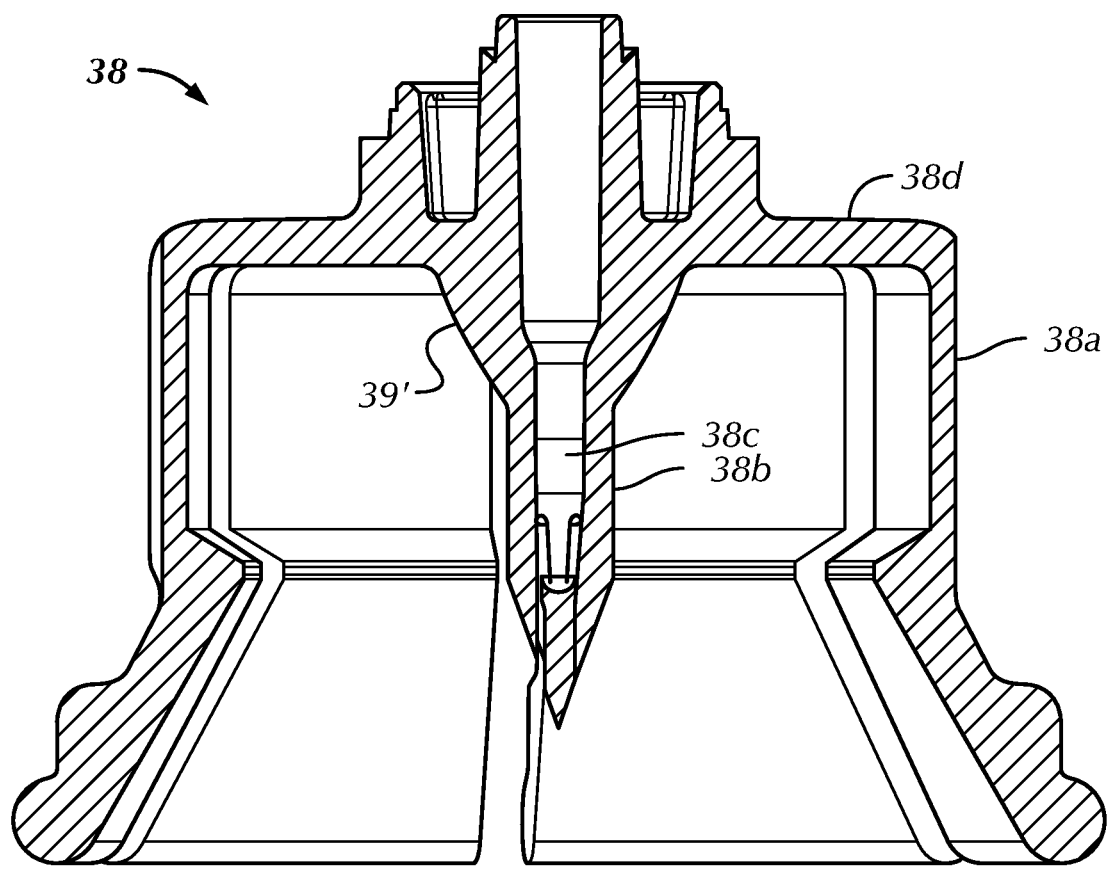
FIG. 7B is an enlarged cross-sectional elevational view of another configuration of a vial adapter of the liquid transfer device of FIG. 2A.

In the configuration of FIG. 7A, the vial spike 38b includes a base section 39 that is generally concave with respect to the axis of the vial spike 38b. The vial adapter 38 may alternatively be configured to minimize/protect against leakage resulting from the tear that forms in the stopper of a vial 20 as the vial adapter 38 is pushed down onto the vial 20 and the vial spike 38b advances through the stopper. As illustrated in the configuration of FIG. 7B, the direction of extension of the base section 39' is generally convex with respect to the axis of the vial spike 38b such that the base section 39' has a generally bulbous configuration. When the vial adapter 38 is pushed down onto the vial 20 and the spike 38b advances through the vial stopper, the base section 39' is compressed against an upper surface of the vial stopper and the compressed material of the vial stopper surrounds tears formed in the vial stopper for sealing thereof. Puncturing of the vial stopper by the vial spike 38b is generally accompanied by the formation of a depression in the upper surface of the vial stopper. The convex base section 39' is configured to fill in the depression, thereby minimizing/protecting against leakage. As should be understood by those of ordinary skill in the art, however, different sealing base sections/means, currently known, or that later become known, may be employed to minimize leakage between the vial spike 38b and the elastic stopper of vial 20. As also should be understood, other vial adapter configurations, currently known, or that later become known, may alternatively be employed.

Turning to the plunger 40, as shown best in FIGS. 2B, 3, 4B and 5, the plunger 40 includes an upright plunger tube 46, defining a plunger tube lumen 46a therein. The plunger tube 46 is slidably engaged with the barrel 34 via a peripheral sealing member 42 (constructed, for example, of an elastomeric material or the like) interposed therebetween in a manner well understood by those of ordinary skill in the art, permitting sliding within the barrel 34 while creating a substantially air-tight seal between the plunger tube 46 and the interior sidewall of the barrel 34. The plunger tube 46 and the sealing member 42, in combination with the barrel 34, define a sealed proximal end of the barrel chamber 34a. The plunger tube 46 includes a distal, elongate neck portion 44 terminating in a check valve 48. In the illustrated embodiment, the check valve 48 takes the form of a duckbill valve, constructed of an elastomeric material or the like, but the disclosure is not so limited. For example, without limitation, the check valve 48 may take the form of several other types of one-way valves, such as, for example, a ball valve, a silicone flapper valve, a diaphragm-type valve, an in-line valve, a stop-check valve, a lift-check valve, or the like, capable of performing the functions of the check valve 48 described herein.

As shown, an IV port 50 is fluidly connected with a proximal end of the plunger tube 46. The IV port 50 includes a twist-off member 50a proximate a peripheral, free proximal end of the port 50, and an elongate connecting member 52 projecting distally therefrom, having an internal lumen 52a extending therethrough and terminating in an open end (opposite end from the twist-off member 50a). The internal lumen 52a of the IV port 50 extends co-directionally and/or coaxially with the plunger lumen 46a. In one embodiment, the IV port 50 may be constructed from a suitable flexible polymeric or plastic material, such as, for example, PVC, and the like. In the illustrated embodiment, the elongate connecting member 52 is adhered, i.e., adhesively bonded, with the plunger tube 46, but the disclosure is not so limited. For example, without limitation, the elongate connecting member 52 may be permanently secured and rotationally fixedly attached to the plunger tube 46 (for example, as described in further detail below with respect to FIGS. 8 to 10).

The IV port 50 includes a septum 50b positioned within the elongate connecting member 52, sealing across the internal lumen 52a. Accordingly, the twist-off member 50a may be removed without leading to flow communication beyond the septum 50b. Flow communication beyond the septum 50b, i.e., with the plunger lumen 46a and beyond, is only achieved upon puncturing the septum 50b (as described in further detail below). The twist off member 50a keeps the IV port 50, and particularly the septum 50b, sterile until use.

Figure 4A:
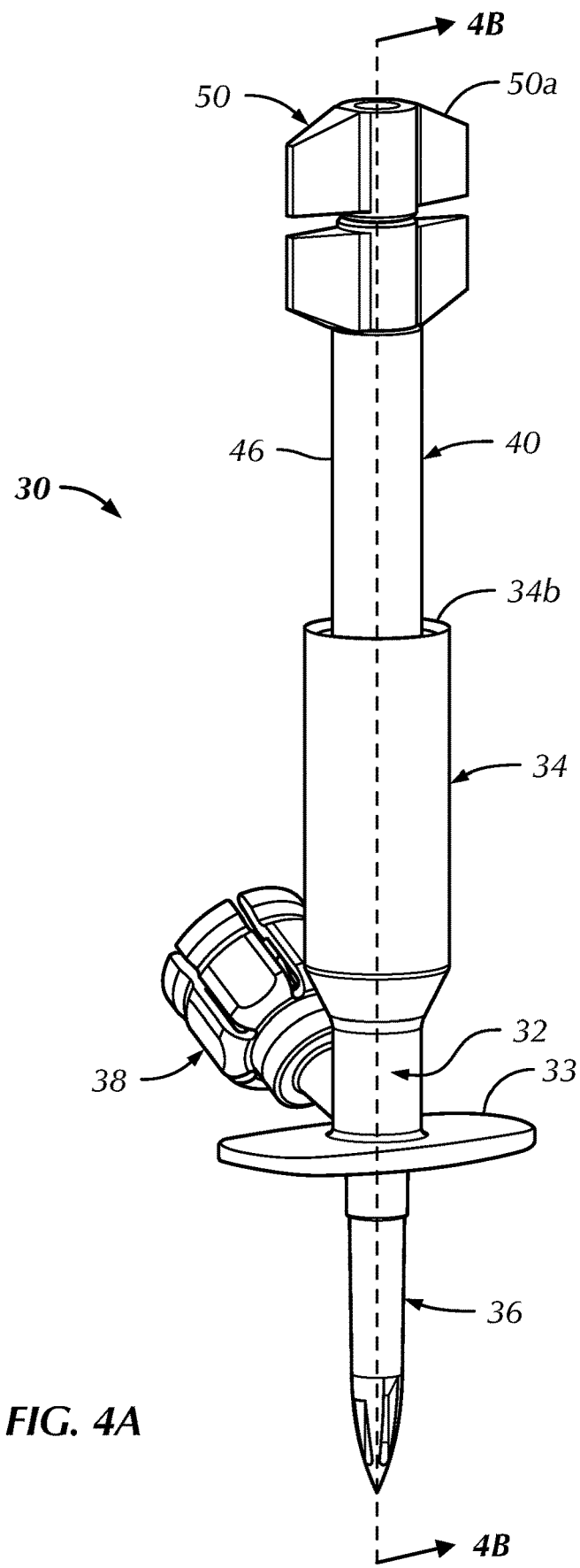
FIG. 4A is a perspective view of the liquid transfer device according to the present disclosure, in a withdrawn plunger configuration.
Figure 4B:
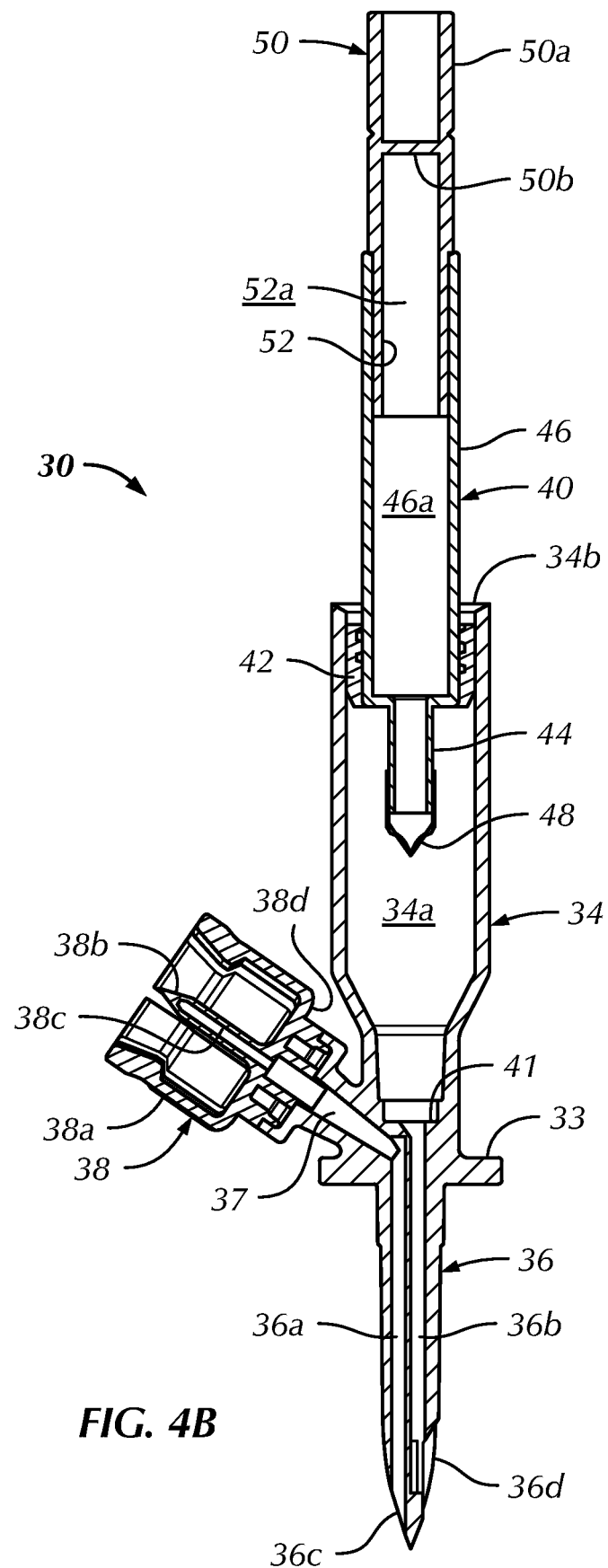
FIG. 4B is a cross-sectional elevational view of the liquid transfer device of FIG. 4A, taken along sectional line 4B-4B of FIG. 4A.

In use, the liquid transfer device 30 may be coupled to an infusion liquid bag 10 via the IV spike 36 (as previously described). Thereafter, the user withdraws the plunger 40 in a proximal direction, i.e. in a direction away from the IV spike 36 (FIGS. 4A, 4B). Alternatively, a dedicated handle may be employed and attached to the plunger 40 for translation thereof. Withdrawal of the plunger 40, with the distal aperture 36*d* immersed in the infusion liquid within the bag 10, pulls fluid from the bag 10, through the distal aperture 36*d*, through the second IV spike lumen 36*b* and into the barrel chamber 34*a*. The duckbill valve 48 is configured to prevent fluid flow into the plunger tube lumen 46*a* during plunger 40 withdrawal. As should be understood by those of ordinary skill in the art, withdrawal of the plunger 40 creates a vacuum in the barrel chamber 34*a*, resulting in a pressure difference relative to the infusion liquid bag 10, thereby pulling the fluid into the barrel chamber 34*a*. As also should be understood, the infusion liquid remains within the barrel chamber 34*a* and the second IV spike lumen 36*b* until manually ejected, in a manner well understood by those of ordinary skill in the art, as will be described below.

Prior or subsequent to withdrawing infusion liquid from the infusion liquid bag 10 into the barrel chamber 34*a*, the liquid transfer device 30 may be coupled to a vial 20 via the vial adapter 38 (as previously described). A user may mix/combine the contents within the vial 20 with the contents within the infusion liquid bag 10 via the vial adapter lumen 37 and the first IV spike lumen 36*a* by inverting the infusion liquid bag 10 and device 30, i.e. positioning the vial 20 above the bag 10, so that the contents of the vial 20 drain into the infusion liquid bag 10. Where the vial 20 contains a lyophilized powder drug, the drug can be reconstituted in a similar fashion. After coupling the vial 20 to the liquid transfer device 30, the liquid bag 10 is held above the vial 20, so that liquid from the liquid bag 10 drains into the vial 20 and reconstitutes the contents of the vial 20. The infusion liquid bag 10 and device 30 may then be inverted, as previously described, to drain the reconstituted contents of the vial 20 into the bag 10.

Figure 1D:
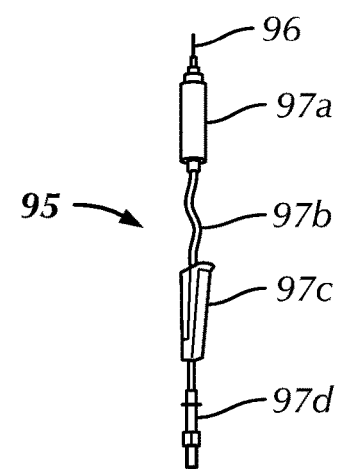
FIG. 1D is a front elevational view of an infusion set usable with the liquid transfer device according to the present disclosure.
Figure 2A:
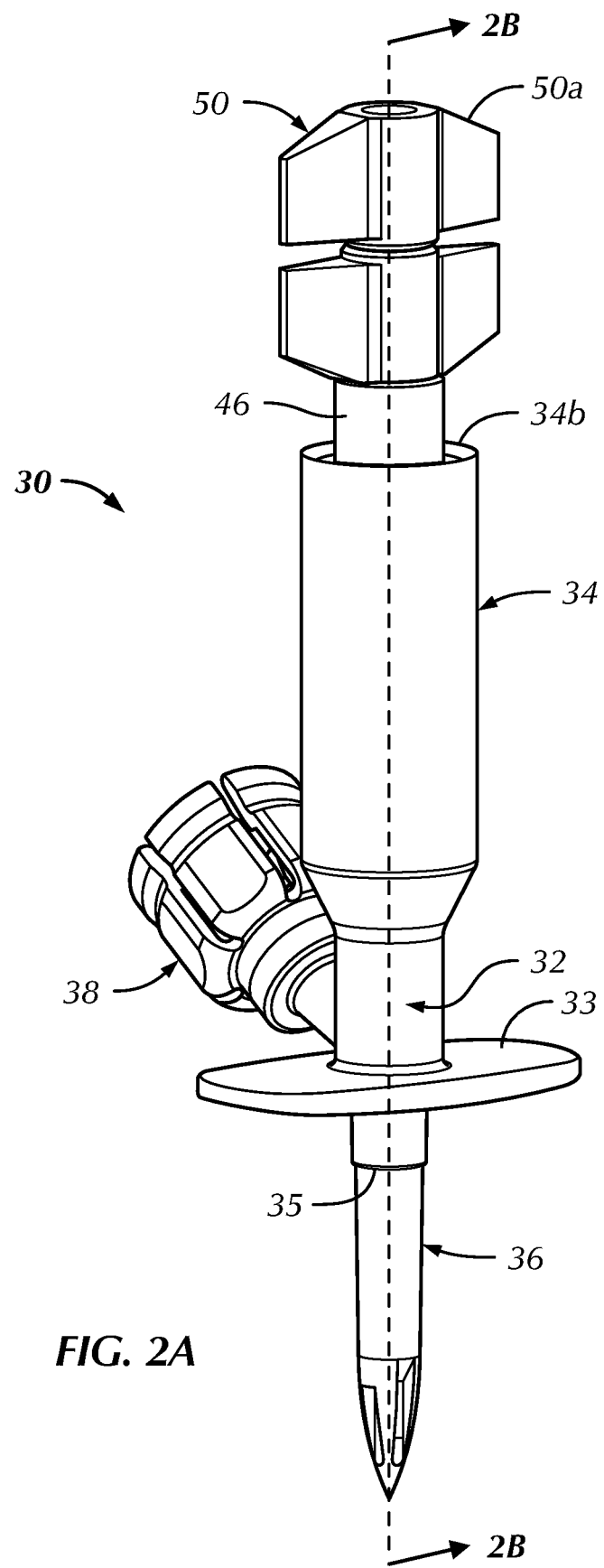
FIG. 2A is a perspective view of the liquid transfer device, in accordance with a first embodiment of the present disclosure, in a depressed plunger configuration.
Figure 2B:
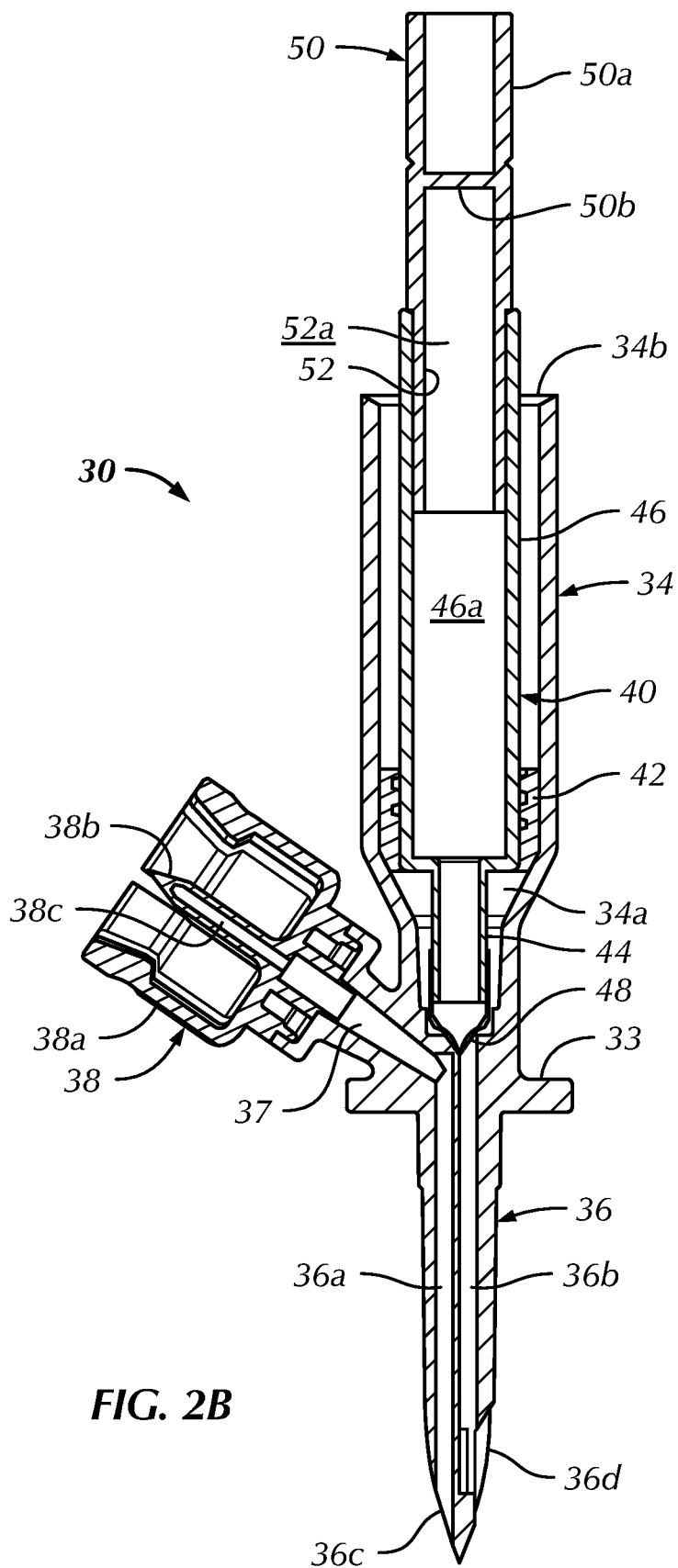
FIG. 2B is a cross-sectional elevational view of the liquid transfer device of FIG. 2A, taken along sectional line 2B-2B of FIG. 2A.
Figure 3:
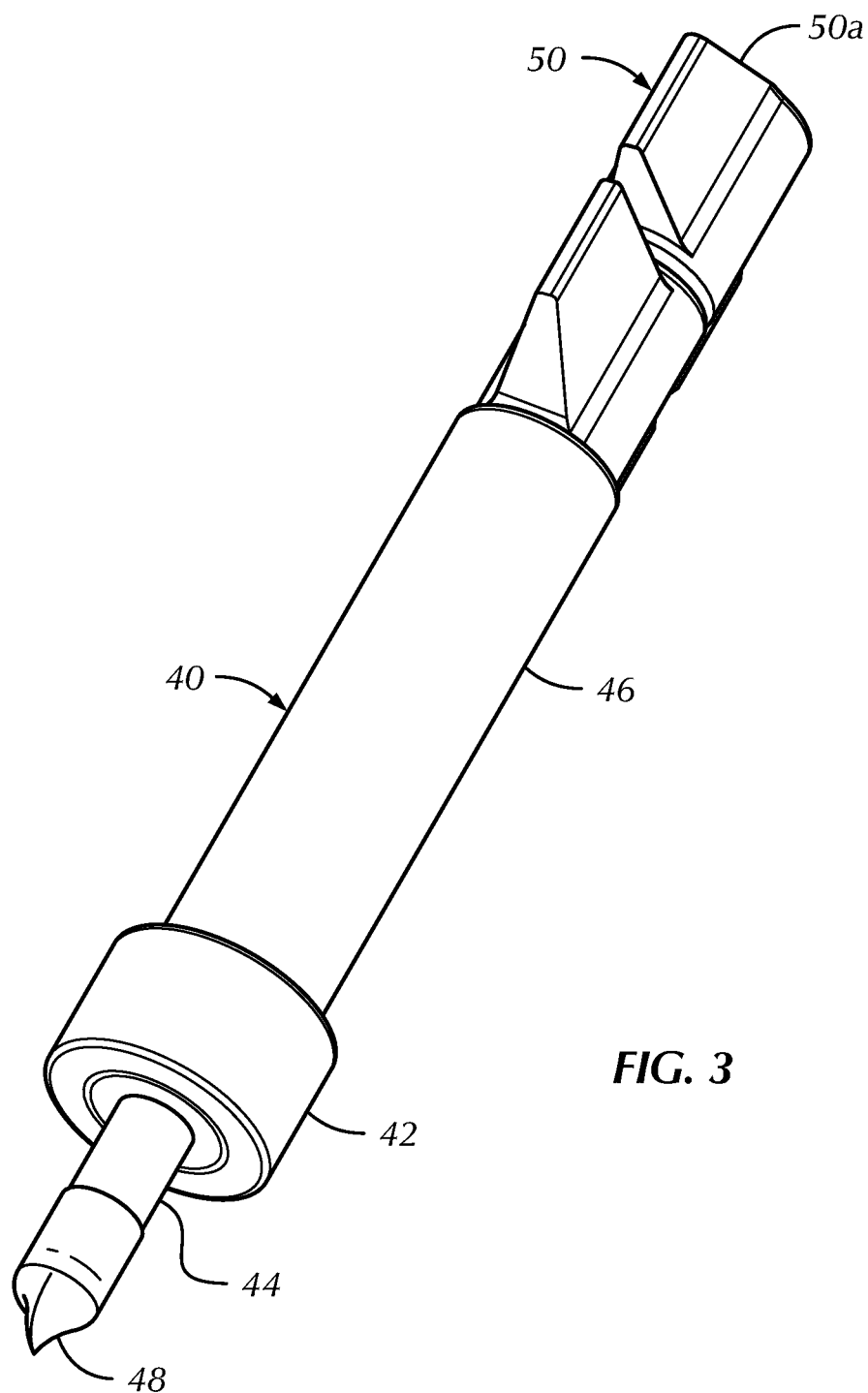
FIG. 3 is a perspective view of the syringe plunger and an IV port of the liquid transfer device of FIG. 2A.

After mixing/combining the contents within the infusion liquid bag 10 and the vial 20 and orienting the liquid transfer device 30 such that the combined liquid flows into the infusion liquid bag 10, the plunger 40 is depressed until at least portion of the duckbill valve 48 engages the proximal end/rim of the second IV spike lumen 36*b*. In the illustrated embodiment, at least one of the elastomeric lips/flaps of the duckbill valve 48 abuts, and is displaced/compressed by, the proximal end 41 of the second IV spike lumen 36*b*, thereby opening the duckbill valve 48 for fluid-flow therethrough. That is, sustained pressure applied onto at least one of the elastomeric lips/flaps of the duckbill valve 48, resulting from the depression of the plunger 40 to a position engaging the valve 48 with the proximal end/rim 41 of the second IV spike lumen 36*b*, displaces the elastomeric lips/flaps of the valve 48 from one another, thereby breaking the seal therebetween and permitting fluid flow therethrough. Thereafter, the twist-off member 50*a* is removed (in a manner well understood) to provide access to the internal lumen 52*a*. An IV port spike 96 of an infusion set 95 (FIG. 1D) is sealingly inserted into the internal lumen 52*a* and fully penetrates the septum 50*b*, thereby fluidly connecting the IV port spike 96 with any remainder of the internal lumen 52*a* beyond the septum 50*b*, and, in turn, with the plunger lumen 46*a* and the second IV spike lumen 36*b* (via the open duckbill valve 48) for administration of the medicated infusion liquid to a patient. The IV port spike 96 typically extends from an end of a drip chamber 97*a* of the infusion set 95. Conventionally, an infusion set 95 additionally includes a roller clamp 97*c* for controlling fluid administration to a patient, a male Luer connector 97*d*, and tubing 97*b* to fluidly connect the roller clamp 97*c* to the drip chamber 97*a*.

Advantageously, the medicated infusion liquid is fluidly connected to the infusion set 95 via the second IV spike lumen 36*b* rather than the first IV spike lumen 36*a*, which is utilized only to admix the highly concentrated drug additive within the vial 20 with the infusion liquid within the bag 10. Thus, the possibility of administering a portion of the drug additive in an undiluted, high concentration form to a patient is minimized. Moreover, as the plunger 40 is depressed (as previously described), infusion liquid within the barrel chamber 34*a* is ejected through the second IV spike lumen 36*b* and out the distal aperture 36*d*. Therefore, after utilizing the liquid transfer device 30 to admix the contents within the infusion liquid bag 10 and the vial 20, the second IV spike lumen 36*b* and the distal aperture 36*d* thereof, though not utilized for mixing, are nevertheless flushed out prior to use thereof for transferring the medicated infusion liquid from the bag 10 to the infusion set 95, to further minimize the possibility of administering a portion of the drug additive in an undiluted, high concentration form to a patient.

Figure 5:
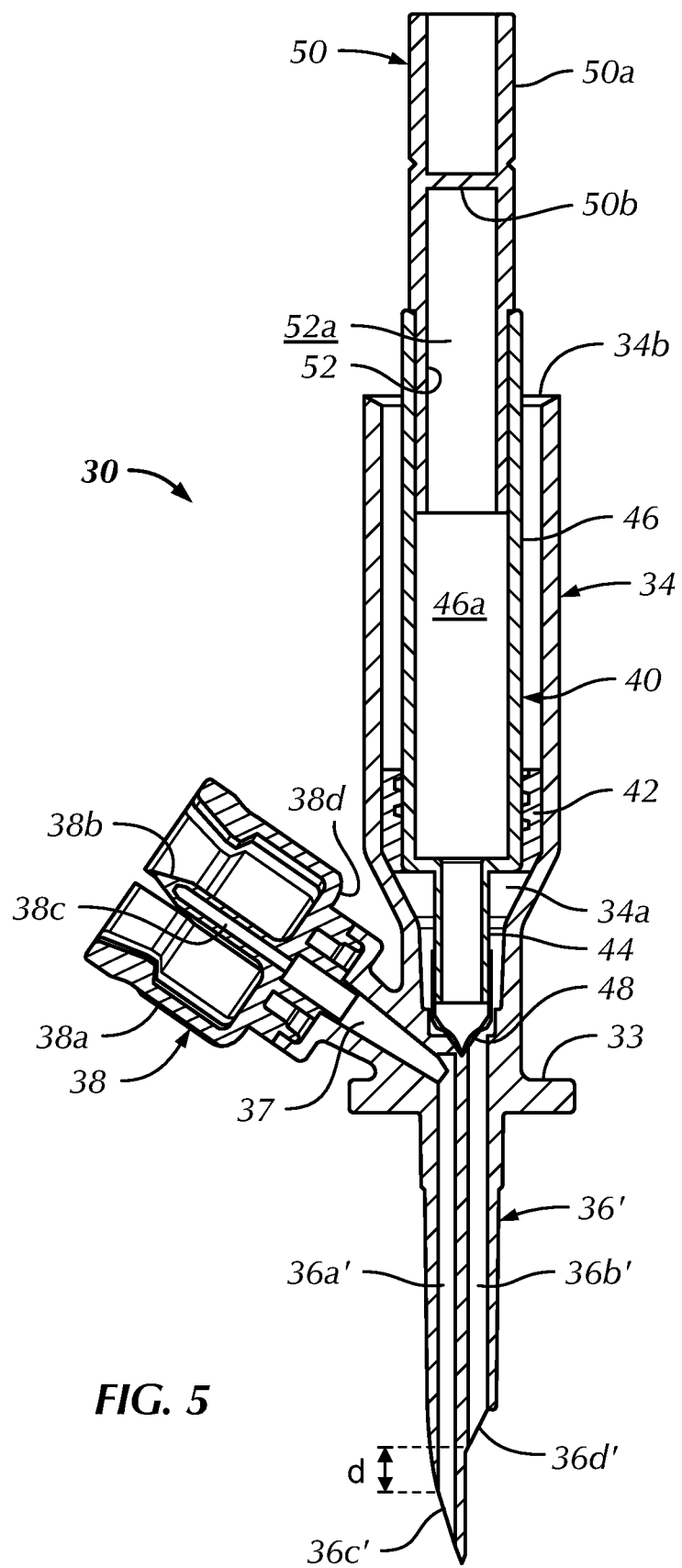
FIG. 5 is a cross-sectional elevational view of another embodiment of a liquid transfer device having an alternatively configured IV spike.

In an alternative configuration, as shown in FIG. 5, a distal end of the IV spike 36' is configured such that the first IV spike lumen 36*a*' extends further distally than the second IV spike lumen 36*b*'. Advantageously, therefore, the first distal aperture 36*c*' is separated by a distance "d" from the distal aperture 36*d*', thereby further minimizing the opportunity for a portion of the drug in an undiluted, high concentration form from exiting the first distal aperture 36*c*' and entering the distal aperture 36*d*'. The distance "d" is preferably greater than or equal to about 1.0 mm, more preferably greater than or equal to about 2.5 mm, and most preferably greater than or equal to about 4.0 mm.

Figure 6:
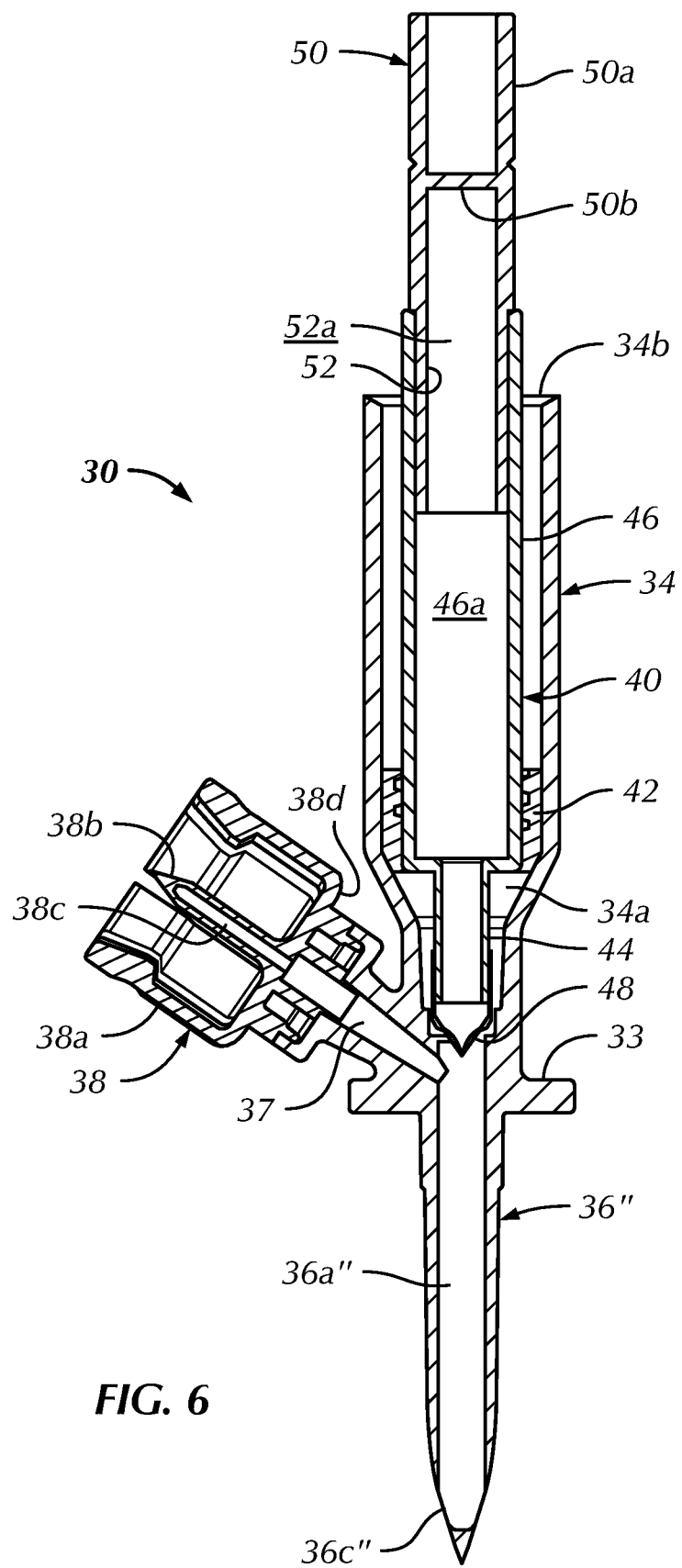
FIG. 6 is a cross-sectional elevational view of the liquid transfer device of FIG. 2A, taken along sectional line 2B-2B of FIG. 2A, having another alternatively configured IV spike.

In another alternative configuration, as shown in FIG. 6, the IV spike 36" may include a single lumen 36*a*" with a single distal aperture 36*c*". This configuration operates in a similar manner as with the configuration shown in FIGS. 2-4B, except that withdrawing/ejecting fluid from or into the barrel chamber 34*a* and mixing the drug with fluid occurs in part through a common portion of the single lumen 36*a*". Flushing of the lumen 36*a*", as previously described, is performed between the steps of mixing/combining the contents within the infusion liquid bag 10 and the vial 20, and removing the twist-off member 50*a* for connection of the infusion set 95.

Figure 11B:
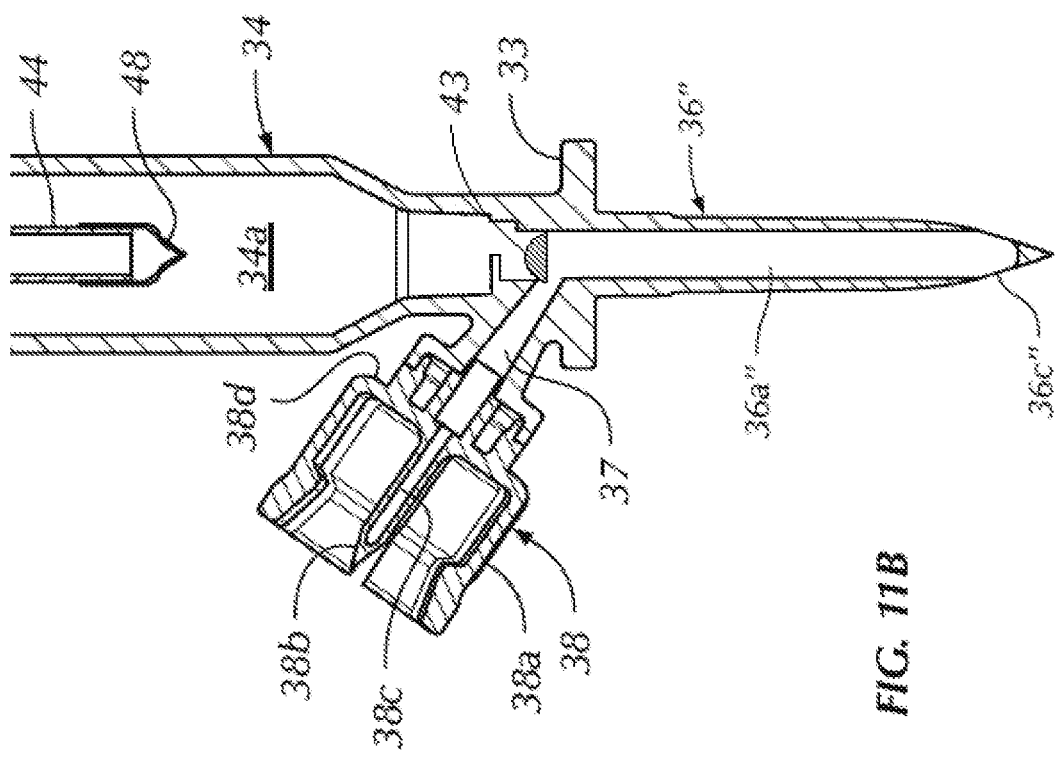
FIGS. 11A and 11B are cross-sectional elevational views of another embodiment of the liquid transfer device of FIG. 6 having an internal valve.
Figure 11A:
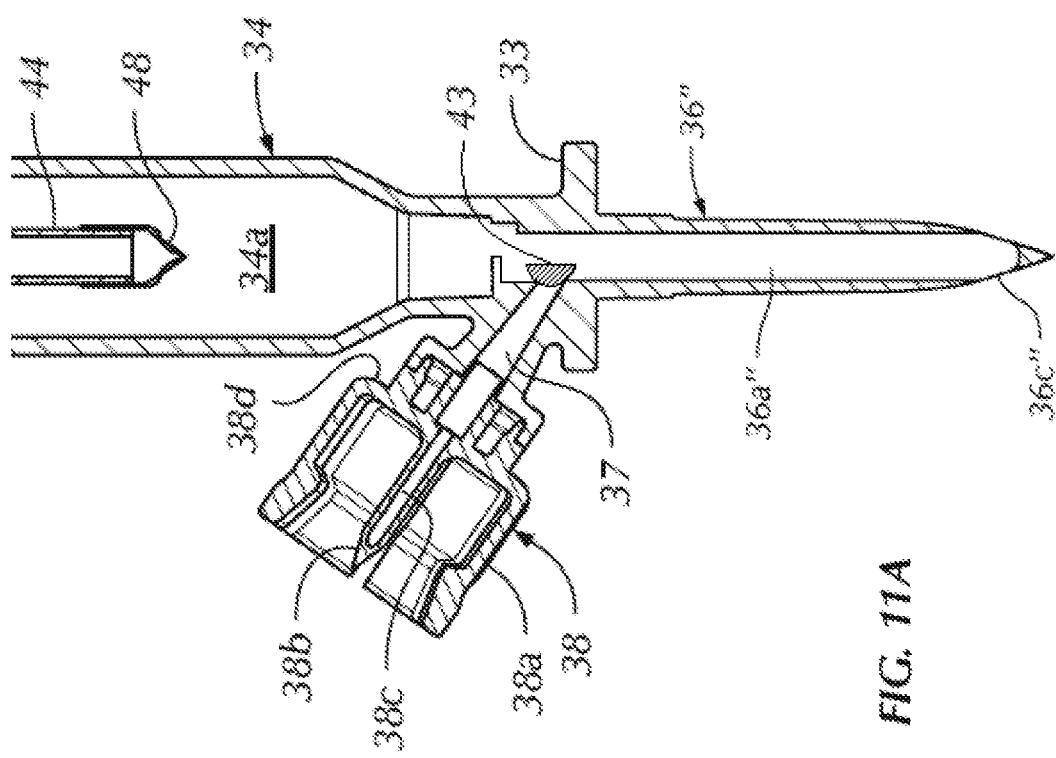

In a preferred embodiment illustrated in FIGS. 11A and 11B, a flow control valve 43 may be incorporated in the device, such that rotation of the flow control valve 43 allows a user to selectively fluidly connect either the vial adapter lumen 37 or the barrel chamber 34*a* with the single lumen 36*a*". The valve 43 may prevent any highly concentrated drug additive within the vial 20 from being drawn into the barrel chamber 34*a* when the plunger tube 46 is withdrawn, as illustrated in FIG. 11A. Prior to mixing the contents of the vial 20 into the bag 10, the valve 43 may be rotated in order to provide a fluid connection between the vial adapter lumen 37 and the single lumen 36*a*", as well as seal off the barrel chamber 34*a*, as illustrated in FIG. 11B. In order to flush the volume of liquid within the single lumen 36*a*", the valve 43 may be rotated back to its original position in FIG. 11A prior to depressing the plunger tube 46.

In another alternative embodiment, the vial adapter 38 may be detachable. For example, the device may be provided with a valve, such as the needleless additive control valve disclosed in U.S. Pat. No. 8,551,067, the contents of which are incorporated by reference herein. The valve would allow the vial adapter 38 to be detached prior to withdrawing the plunger tube 46. The vial adapter 38 and vial 20 would then be connected via the valve to empty the highly concentrated contents of the vial 20 into the bag 20 followed by depression of the plunger tube 46 to flush the single lumen 36*a*".

Figure 8:
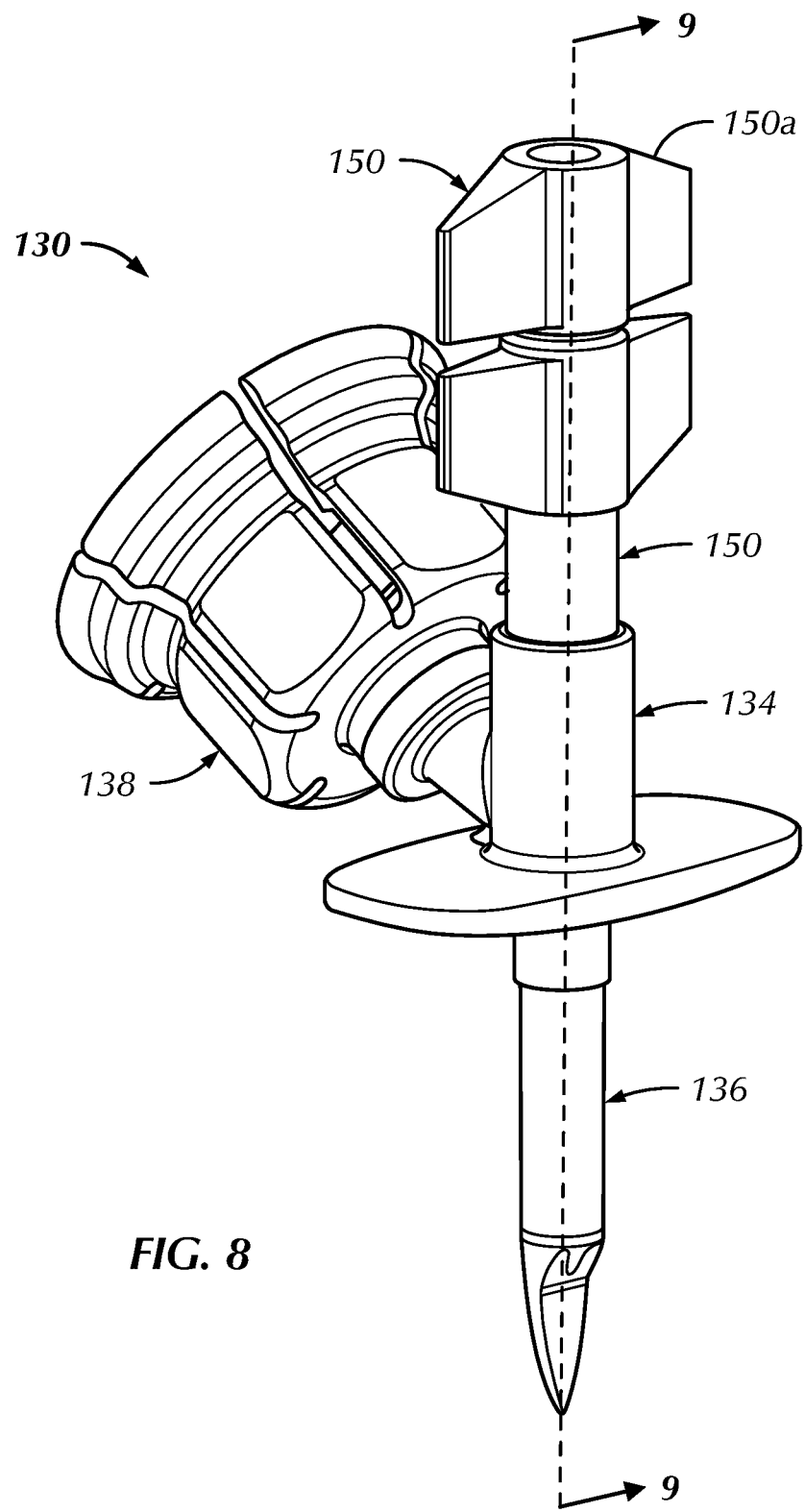
FIG. 8 is a perspective view of a liquid transfer device, in accordance with a second embodiment of the present disclosure.
Figure 9:
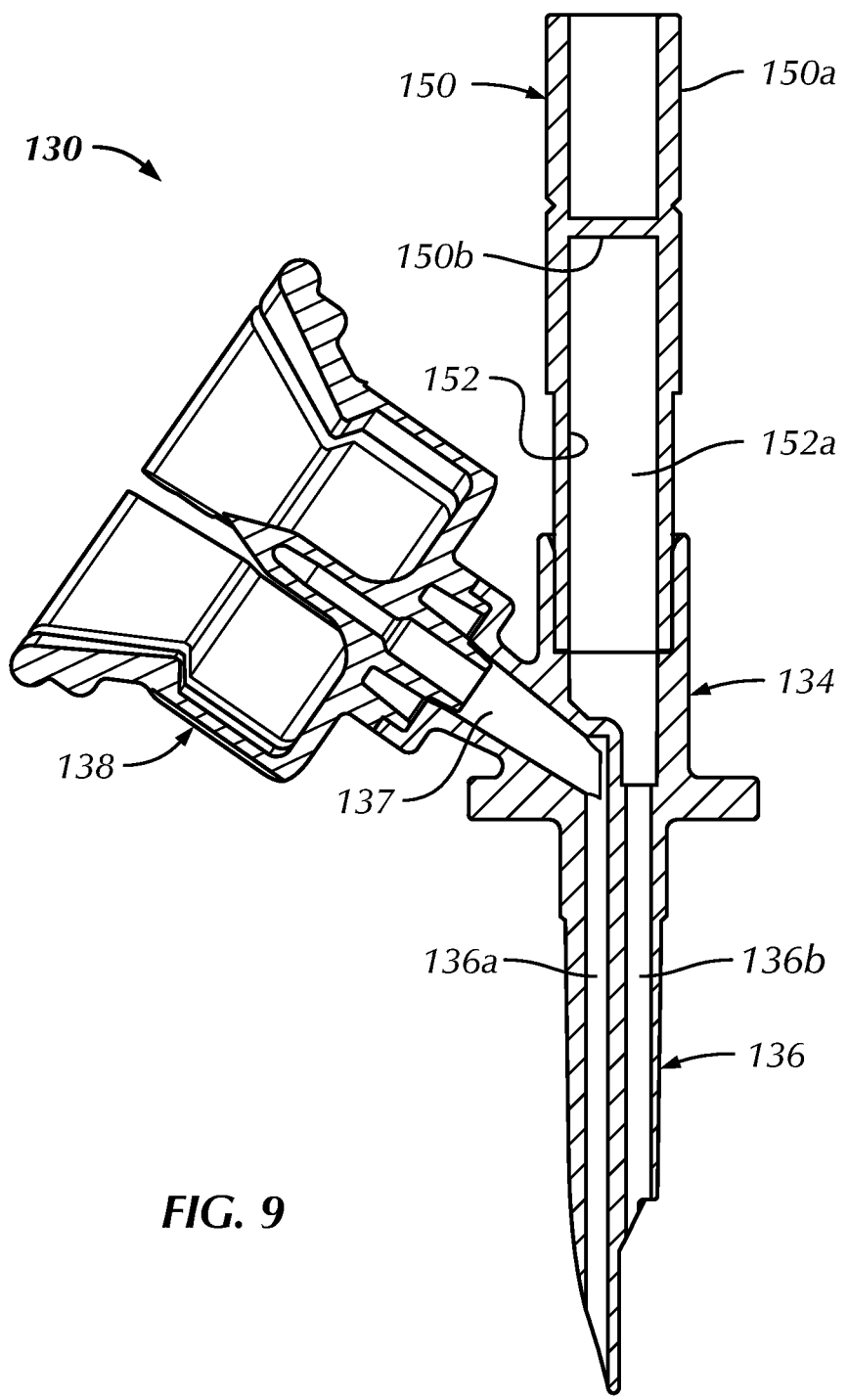
FIG. 9 is a cross-sectional elevational view of the liquid transfer device of FIG. 8, taken along sectional line 9-9 of FIG. 8.
Figure 10:
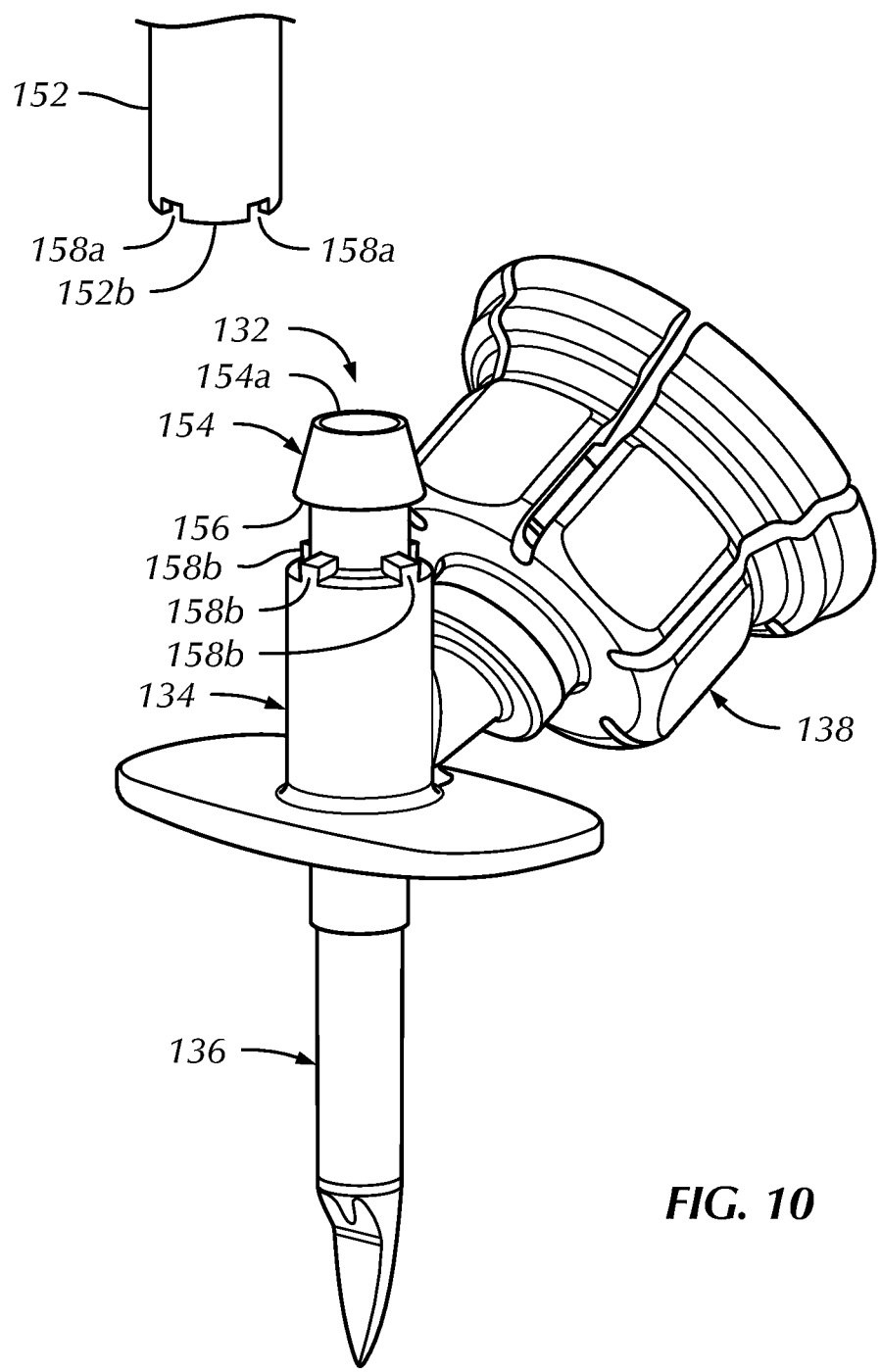
FIG. 10 is an enlarged partial, exploded, perspective view of an alternative attachment between a trifurcated connector body and an elongate connecting member, such as an IV port, of the liquid transfer device of FIG. 8.

FIGS. 8-10 illustrate a second embodiment of the liquid transfer device 130. The reference numerals of the second embodiment are distinguishable from those of the above-described first embodiment configurations (FIGS. 2A-7B) by a factor of one-hundred (100), but otherwise indicate the same elements as indicated above, except as otherwise specified. The liquid transfer device 130 of the present embodiment is similar to that of the first embodiment configurations. Therefore, the description of certain similarities and modes of operation between the embodiments may be omitted herein for the sake of brevity and convenience, and, therefore, is not limiting.

One difference of the liquid transfer device 130 over the liquid transfer device 30 pertains to the configuration of the first end of connector body 132. As shown in FIGS. 8 and 9, the plunger 40 is removed and the IV port 150 is directly and permanently secured and sealed to the barrel 134, i.e., not disconnectable/removable without causing damage to at least one of the IV port 150 or the barrel 134 or otherwise to the device 130. Accordingly, the second IV spike lumen 136b of the single IV spike 136 is in direct and continuous fluid communication at a proximal end with only the internal lumen 152a of the elongate connecting member 152 of the IV port 150, while remaining not fluidly connected at the proximal end thereof with the vial adapter lumen 137. The first IV spike lumen 136a of the single IV spike 136 also remains continuously and directly fluidly connected at a proximal end with only the vial adapter lumen 137 and not fluidly connected at the proximal end thereof with the internal lumen 152a of the elongate connecting member 152.

In the illustrated embodiment of FIGS. 8 and 9, the elongate connecting member 152 is adhered, i.e., adhesively bonded, with the barrel 134. As previously noted, the elongate connecting member 152 may be permanently secured attached to the barrel 134. For example, as shown in FIG. 10, the barrel 134 may terminate in a barbed fitting member 154 having an open end 154a. The barbed fitting member 154 may be configured, i.e., size, dimension, material, relative to the internal diameter and material of the elongate connecting member 152 to advance into the internal lumen 152a and form a barbed, friction, i.e., interference, fit therebetween. As should be understood by those of ordinary skill in the art, the orientation of the barbed fitting member 154 permits advancement thereof into the internal lumen 152a to sealingly and securely mount the IV port 150 co-directionally upon the barrel 134 of the connector body 132, and also substantially prevent withdrawal of the barbed fitting member 154 without damaging at least one of the elongate connecting member 152 and the barbed fitting member 154.

As shown, the barbed fitting member 154 is frustoconically shaped, having a progressively increasing diameter in a direction away from the open end 154a. An opposing end of the barbed fitting member 154 defines a greater diameter from the underlying portion of the barrel 134, resulting in an annular rib 156 that provides an interference fit with the interior sidewall of the elongate connecting member 152, upon attempted withdrawal of the barbed fitting member 154 out of the elongate connecting member 152. Accordingly, the barbed fitting member 154 is advanceable into the internal lumen 152a of the elongate connecting member 152 during assembly, and, thereafter, is not readily able to be withdrawn without causing damage.

Additionally, the rim of the elongate connecting member 152 defining an open end 152b thereof includes at least one cutout 158a, and the barrel 134 includes a corresponding at least one radial tab 158b protruding from the barrel 134 and configured to mate with the at least one cutout 158a. In the illustrated embodiment, the elongate connecting member 152 includes a plurality of angularly spaced cutouts 158a, and the barrel 134 includes a corresponding plurality of angularly spaced tabs 158b. The tab(s) 158b mates with the cutout(s) 158a during mounting of the IV port 150 upon the barbed fitting member 154 of the barrel 134, to rotationally fix the IV port 150 relative to the remainder of the liquid transfer device 130. The tab(s) 158b also prevent relative rotation between the barrel 134 and the elongate connecting member 152 and enable a twist-off member 150a to be removed, as noted below, prior to connection to the infusion set 95.

In use, the liquid transfer device 130 may be coupled to a vial 20 via the vial adapter 138 and the user may mix/combine the contents within the vial 20 with the contents within the infusion liquid bag 10, via the vial adapter lumen 137 and the first IV spike lumen 136a. After mixing/combining the contents within the infusion liquid bag 10 and the vial 20 and orienting the liquid transfer device 130 such that the combined liquid flows into the infusion liquid bag 10, the twist-off member 150a is removed (in a manner well understood) to provide access to the internal lumen 152a and the IV port spike 96 of an infusion set 95 (FIG. 1D) is sealingly inserted into the internal lumen 152a and fully penetrates the septum 150b, thereby fluidly connecting the IV port spike 96 with any remainder of the internal lumen 152a beyond the septum 150b, and, in turn, with the second IV spike lumen 136b for administration of the medicated infusion liquid to a patient.

It will be appreciated by those skilled in the art that changes could be made to the embodiments described above without departing from the broad inventive concepts thereof. For example instead of a vial adapter, the trifurcated connector body 32, 134 may include a normally closed (NC) needleless additive port (not shown) at the third end thereof (enabling selection of use with a syringe 22 or with a vial 20). As another example, the vial adapter 38, 138 can be replaced by a manually operated stop cock, and the like. As yet another example, the liquid transfer device 30 may include a locking mechanism to stabilize and/or lock the plunger 40 in the different positions thereof. It is understood, therefore, that this invention is not limited to the particular embodiments disclosed, but it is intended to cover modifications within the spirit and scope of the present disclosure, as set forth in the appended claims.

We claim:

1. A liquid transfer device configured for use with each of an infusion liquid container containing an infusion liquid and having an intravenous administration port for administering the infusion liquid, a vial containing a medicament additive sealed by a vial stopper, and an infusion set including an IV port spike and a connector for administration purposes to a patient, the liquid transfer device comprising:
a monolithic trifurcated connector body defining a barrel at a first end thereof, an IV spike at a second end thereof and a vial adapter lumen at a third end thereof;
an IV port connected to the barrel and configured to sealingly receive the IV port spike of the infusion set; and
a vial adapter configured to telescopically mount onto the vial, the vial adapter including a vial spike fluidly connected with the vial adapter lumen and configured to puncture the vial stopper upon mounting of the vial adapter onto the vial for flow communication therewith, the IV spike being configured to sealingly insert into the intravenous administration port of the infusion liquid container, and the IV spike having:
- a first IV spike lumen fluidly connected at a proximal end thereof with the vial adapter lumen via the monolithic trifurcated connector body, the first IV spike lumen having a first peripherally disposed distal aperture; and
- a second IV spike lumen fluidly connected at a proximal end thereof with the IV port via the monolithic trifurcated connector body, the second IV spike lumen having a second peripherally disposed distal aperture,
- thereby separating fluid communication between the vial adapter and the IV spike from fluid communication between the IV port and the IV spike while enabling initial introduction of the medicament additive from the vial to the infusion liquid container through the vial adapter and the first IV spike lumen for mixing with the infusion liquid to form a medicated infusion liquid, and enabling subsequent administration of the medicated infusion liquid to the patient from the infusion liquid container through the second IV spike lumen and the IV port to the infusion set,
- wherein the first IV spike lumen extends further distally than the second IV spike lumen, the first peripherally disposed distal aperture and the second peripherally disposed distal aperture are non-overlapping longitudinally, and the first peripherally disposed distal aperture is distally separated from the second peripherally disposed distal aperture by at least about 1.0 mm.

2. The liquid transfer device of claim 1, wherein the first IV spike lumen is directly and continuously fluidly connected with the vial adapter lumen and the infusion liquid container.

3. The liquid transfer device of claim 2, wherein the second IV spike lumen is directly and continuously fluidly connected with the IV port and the infusion liquid container.

4. The liquid transfer device of claim 1, wherein the IV port is permanently secured to the barrel.

5. The liquid transfer device of claim 1, further comprising a plunger including a plunger tube defining a plunger tube lumen therein,
- wherein the barrel defines an internal chamber fluidly connected with the second IV spike lumen and sealingly and slidably receiving the plunger tube.

6. The liquid transfer device of claim 5, wherein the plunger tube is fluidly connected with the IV port via a proximal end thereof and the plunger tube includes a check valve at a distal end thereof, whereby the IV port is fluidly connected with the second IV spike lumen in an open position of the check valve and fluidly disconnected from the second IV spike lumen in a closed position of the check valve.

7. The liquid transfer device of claim 5, wherein the first IV spike lumen and the second IV spike lumen extend parallel to one another.

8. A method of using a liquid transfer device having a monolithic trifurcated connector body defining a barrel at a first end thereof, a single intravenous (IV) spike at a second end thereof and a vial adapter lumen at a third end thereof, the method comprising:
- mounting a vial adapter comprising the vial adapter lumen onto a vial containing a medicament additive, and piercing a stopper of the vial with a vial spike of the vial adapter fluidly connected with the vial adapter lumen;
- piercing an administration port of an infusion liquid container containing an infusion liquid with the IV spike;
- adding the medicament additive within the vial to the infusion liquid within the infusion liquid container to obtain a medicated infusion liquid via the vial adapter lumen and a first IV spike lumen of the IV spike, the first IV spike lumen being fluidly connected at a proximal end thereof with the vial adapter lumen and having a first peripherally disposed distal aperture proximate a distal end of the IV spike; and
- inserting an IV port spike of an infusion set into an IV port of the liquid transfer device, the IV port of the liquid transfer device being fluidly connected to a second IV spike lumen of the IV spike, wherein the second IV spike lumen is fluidly connected at a proximal end thereof with the IV port and having a second peripherally disposed distal aperture proximate the distal end of the IV spike, thereby fluidly connecting the infusion set with the infusion liquid container for administration of the medicated infusion liquid to a patient, and wherein the first IV spike lumen extends further distally than the second IV spike lumen, the first peripherally disposed distal aperture and the second peripherally disposed distal aperture are non-overlapping longitudinally, and the first peripherally disposed distal aperture is distally separated from the second peripherally disposed distal aperture by at least about 1.0 mm.

9. The method of claim 8, wherein the first IV spike lumen extends further distally than the second IV spike lumen, whereby the first peripherally disposed distal aperture is distally spaced from the second peripherally disposed distal aperture along the IV spike.

10. A liquid transfer device configured for use with each of an infusion liquid container containing an infusion liquid and having an intravenous administration port for administering the infusion liquid, a vial containing a medicament additive sealed by a vial stopper, and an infusion set including an IV port spike and a connector for administration purposes to a patient,
the liquid transfer device comprising:
- a monolithic trifurcated connector body defining a barrel at a first end thereof, an IV spike at a second end thereof and a vial adapter lumen at a third end thereof;
- an IV port connected to the barrel and configured to sealingly receive the IV port spike of the infusion set;
- a vial adapter comprising the vial adapter lumen and configured to telescopically mount onto the vial, the vial adapter including a vial spike fluidly connected with the vial adapter lumen and configured to puncture the vial stopper upon mounting of the vial adapter onto the vial for flow communication therewith,
- the IV spike comprising an IV spike lumen and being configured to sealingly insert into the intravenous administration port of the infusion liquid container; and
- a plunger including a plunger tube defining a plunger tube lumen therein, wherein the barrel defines an internal chamber fluidly connected with the IV spike lumen and sealingly and slidably receiving the plunger tube,
- wherein the plunger tube is fluidly connected with the IV port via a proximal end thereof, and the plunger tube includes a check valve at a distal end thereof, whereby the IV port is fluidly connected with the IV spike lumen in an open position of the check valve and fluidly disconnected from the IV spike lumen in a closed position of the check valve.

11. The liquid transfer device of claim 10, further comprising a flow control valve configured to selectively fluidly connect the IV spike lumen to the vial adapter lumen or the barrel.

12. The liquid transfer device of claim 10, wherein the vial adapter is detachable.

13. The liquid transfer device of claim 1, wherein the vial adapter is detachable.

14. The liquid transfer device of claim 1, wherein the IV spike has a flat surface distal of the second peripherally disposed distal aperture.

15. A liquid transfer device configured for use with each of an infusion liquid container containing an infusion liquid and having an intravenous administration port for administering the infusion liquid, a vial containing a medicament additive sealed by a vial stopper, and an infusion set including an IV port spike and a connector for administration purposes to a patient, the liquid transfer device comprising:
- a monolithic trifurcated connector body defining a barrel at a first end thereof, an IV spike at a second end thereof and a vial adapter lumen at a third end thereof;
- an IV port connected to the barrel and configured to sealingly receive the IV port spike of the infusion set;
- a vial adapter configured to telescopically mount onto the vial, the vial adapter including a vial spike fluidly connected with the vial adapter lumen and configured to puncture the vial stopper upon mounting of the vial adapter onto the vial for flow communication therewith,
- the IV spike being configured to sealingly insert into the intravenous administration port of the infusion liquid container, and the IV spike having:
  - a first IV spike lumen fluidly connected at a proximal end thereof with the vial adapter lumen via the monolithic trifurcated connector body, the first IV spike lumen having a first peripherally disposed distal aperture; and
  - a second IV spike lumen fluidly connected at a proximal end thereof with the IV port via the monolithic trifurcated connector body, the second IV spike lumen having a second peripherally disposed distal aperture,
- thereby separating fluid communication between the vial adapter and the IV spike from fluid communication between the IV port and the IV spike while enabling initial introduction of the medicament additive from the vial to the infusion liquid container through the vial adapter and the first IV spike lumen for mixing with the infusion liquid to form a medicated infusion liquid, and enabling subsequent administration of the medicated infusion liquid to the patient from the infusion liquid container through the second IV spike lumen and the IV port to the infusion set; and
- a plunger including a plunger tube defining a plunger tube lumen therein,
- wherein the barrel defines an internal chamber fluidly connected with the second IV spike lumen and sealingly and slidably receiving the plunger tube.

16. The liquid transfer device of claim 15, wherein the plunger tube is fluidly connected with the IV port via a proximal end thereof, and the plunger tube includes a check valve at a distal end thereof, whereby the IV port is fluidly connected with the second IV spike lumen in an open position of the check valve and fluidly disconnected from the second IV spike lumen in a closed position of the check valve.

17. The liquid transfer device of claim 15, wherein the first IV spike lumen and the second IV spike lumen extend parallel to one another.

18. The liquid transfer device of claim 15, wherein the vial adapter is detachable.

* * * * *